(12) United States Patent
Motterlini et al.

(10) Patent No.: US 7,045,140 B2
(45) Date of Patent: May 16, 2006

(54) THERAPEUTIC DELIVERY OF CARBON MONOXIDE

(75) Inventors: Roberto Angelo Motterlini, Middlesex (GB); Brian Ernest Mann, Sheffield (GB)

(73) Assignee: Hemocorm Limited, London (GB)

( * ) Notice: Subject to any disclaimer, the term of this patent is extended or adjusted under 35 U.S.C. 154(b) by 384 days.

(21) Appl. No.: 10/143,824

(22) Filed: May 14, 2002

(65) Prior Publication Data

US 2003/0064114 A1 Apr. 3, 2003

(30) Foreign Application Priority Data

May 15, 2001 (GB) ................................. 0111872.8

(51) Int. Cl.
*A61F 2/02* (2006.01)
*A61F 13/02* (2006.01)
*A61K 9/48* (2006.01)
*A61K 9/20* (2006.01)

(52) U.S. Cl. ...................... 424/423; 424/434; 424/435; 424/436; 424/451; 424/464

(58) Field of Classification Search ................ 424/423, 424/434, 435, 436, 451, 464
See application file for complete search history.

(56) References Cited

U.S. PATENT DOCUMENTS 5,882,674 A * 3/1999 Herrmann et al. .......... 424/448
2002/0155166 A1 10/2002 Choi et al.

FOREIGN PATENT DOCUMENTS

| HU | 211 084 B | 4/1990 |
|---|---|---|
| WO | WO 91/01128 | 2/1991 |
| WO | WO 91/01301 | 2/1991 |
| WO | WO 94/22482 | 10/1994 |
| WO | WO 95/05814 | 3/1995 |
| WO | WO 98/29115 | 7/1998 |
| WO | WO 98/48848 | 11/1998 |
| WO | WO 00/56743 | 9/2000 |
| WO | WO 02/078684 | 10/2002 |
| WO | WO 02/080923 | 10/2002 |
| WO | WO 03/000114 | 1/2003 |
| WO | WO 03/0666067 | 8/2003 |
| WO | WO 03/072024 | 9/2003 |
| WO | WO 03/088923 | 10/2003 |
| WO | WO 03/088981 | 10/2003 |
| WO | WO 03/094932 | 11/2003 |

OTHER PUBLICATIONS

Furchgott, et al, Blood Vessels 1991;28:52-61 "Endothelium-Dependent and -Independent Vasodilation Involving Cyclic GMP: Relaxation Induced by Nitric Oxide, Carbon Monoxide and Light".

Wang et al, Biochemistry, vol. 18, No. 22, 1979, 4960-4977 "A Correlation of the Visible and Soret Spectra of Dioxygen- and Carbon Monoxide-Heme Complexes and Five-Coordinate Heme Complexes with the Spectra of Oxy-, Carboxy-, and Deoxyhemoglobins".

(Continued)

*Primary Examiner*—Carlos A. Azpuru
(74) *Attorney, Agent, or Firm*—Nixon & Vanderhye P.C.

(57) ABSTRACT

Metal carbonyls are used to deliver CO having biological activity, for example vasodilatation and inhibition of transplant rejection. The metal of the carbonyl is typically of groups 7 to 10, e.g. Fe and Ru. The carbonyl preferably has one or more ligands other than CO, such as amino acids, to modulate the CO release property and solubility.

31 Claims, 17 Drawing Sheets

Iron pentacarbonyl
[Fe(CO)₅]

Dimanganese decacarbonyl
[Mn₂(CO)₁₀]

OTHER PUBLICATIONS

Schubert, Nov., 1933 Carbon Monoxide on Iron and Cobalt Cysteine Complexes, vol. 55, 4563-4570 "The Action of Carbon Monoxide on Iron and Cobalt Complexes of Cysteine".

Carroll et al, Can. J. Chem. vol. 52, 1974, 1914-1922 "Ligand Abstraction in the Reaction of Aryldiazonium Ions with some Iron Complexes Containing Coordinated Cysteine, Maleonitriledithiol, or Triarylphosphine".

Sjöstrand, Scan. J. Clin. Lab Invest., 1949, 1:201-214 "Endogenous Formation of Carbon Monoxide In Man Under Normal and Pathological Conditions".

Coburn et al, J. of Clinical Investigation, vol. 42, No. 7, 1963, 1172-1178 "Endogenous Carbon Monoxide Production in Man".

Tenhunen et al, J. of Biological Chemistry, vol. 244, No. 23, 6388-6394 (1969) "Microsomal Heme Oxygenase".

Maines, Dept. of Biophysics, University of Rochester, FASEB J 2:2557-2568 (1988) "Heme oxygenase: function, multiplicity, regulatory mechanisms, and clinical applications".

Morita et al, Proc. Natl. Acad. Sci. USA, Cell Biology, 1995, vol. 92, 1475-1479, "Smooth muscle cell-derived carbon monoxide is a regulator of vascular cGMP".

Sammut et al, British J. of Pharmacology, 1998, 125, 1437-1444 "Carbon monoxide is a major contributor to the regulation of vascular tone in aortas expressing high levels of haeme oxygenase-1".

Maines, Annu. Rev., Pharmacol. Toxocol, 1997, 517-554, "The Heme Oxygenase System: A Regulator of Second Messenger Gases".

Soares et al, Nature Medicine, vol. 4, No. 9, 1998, 1073-1077, "Expression of heme oxygenase-1 can determine cardiac xenograft survival".

Willis et al, Nature Medicine, vol. 2, No. 1, 1996, 87-90 "Heme oxygenase: A novel target for the modulation of the inflammatory response".

Motterlini et al, Regulation of Pressor Responses by HO-1-Derived CO, 1998, 568-577 "Heme Oxygenase-1-Derived Carbon Monoxide Contributes to the Suppression of Acute Hypertensive Responses In Vivo".

Otterbein et al, Am. J. Physiol., 1999, 688-694 Carbon monoxide provides protection against hyperoxic lung injury.

Otterbein et al, J. Clin. Invest., 103; 1047-1054, 1999, "Exogenous administration of heme oxygenase-1 by gene transfer provides protection against hyperoxia-induced lung injury".

Herrick et al, Inorg. Chem. 1984, 23, 4550-4553 "Flash Photolytic Investigation of Photoinduced Carbon Monoxide Dissociation from Dinuclear Manganese Carbonyl Compounds".

Alessio et al, Inorg. Chem., 1995, 34, 4722-4734 "Carbonyl Derivatives of Chloride-Dimethyl Sulfoxide-Ruthenium (II) Complexes: Synthesis, Structural Characterization, and Reactivity of $RU(CO)_x(DMSO)_{4-x}Cl_2$ Complexes (x=1-3)".

Sato et al, The J. of Immunology, 2001, 4185-4195, "Carbon Monoxide Generated by Heme Oxygenase-1 Suppresses the Rejection of Mouse-to-Rat Cardiac Transplants".

Pneumatikakis et al, Inorganica Chimica Acta, 151, 1988, 243-248 "Interactions of Bis-[μ-chloro-chlorotricarbonylruthenium(II) and poly-[μ-dichloro-dicarbonylruthenium (II) with Nucleotides".

Yan et al, Pharmazie, 2000, 55(4), 307-313 "Cytotoxicity of rhenium (I) alkoxo and hydroxo carbonyl complexes in murin and human tumor cells".

Becker et al, Medical Sciences (1979), vol. 15, No. 2, 147-150, "Age related changes in antibody dependent cell mediated cytotoxicity in mouse spleen".

Nagai et al., Biochemistry, 1991, vol. 30, No. 26, 6495-6503, "Unusual CO Bonding Geometry in Abnormal Subunits of Hemoglobin M Boston and Hemoglobin M Saskatoon".

Tomita et al., Inorganic and Nuclear Chemistry Letters 1968, vol. 4, 715-718 "Structure and Reaction of Bis(L-cysteinato)Dicarbonyliron(II)".

Ferrier et al, J. of Molecular Structure 344, 1995, 189-193 "FTIR spectrometric study of geometrical isomers of dicarbonyl ferrobiscysteinate Influence of the counter cation".

Szakács-Schmidt et al, Inorganica Chimica Acta, 198-200, 1992, 401-405 "Iron (II) thiolates as reversible-carbon monoxide carriers".

Takács et al, Inorganic Chimica Acta, 166, 1989, 39-46 "Synthesis and Molecular Structure of Carbonyl Derivatives of Iron(II) Thiolates Containing Nitrogen-donor Ligands".

Tomita et al, Inorg. Nucl. Chem. Letters vol. 4, 715-718, 1968, "Structure and Reaction of Bis(L-cysteinato)Dicarbonyliron(II)".

Huang et al, J. Am. Chem. Soc., 1991, 113, 9141-9144 "Photolysis of the Histidine-Heme-CO Complex".

Silver et al, Inorganica Chimica Acta, 91, 1984, 279-283 "Mossbauer Studies on Protoprophyrin IX Iron(II) Solutions Containing Sulphur Ligands and their Carbonyl Adducts. Models for the Active Site of Cytochromes P-450".

Diamantis et al, Inorg. Chem., 1981, 20, 1141-1150 Preparation and Structure of Ethylenediaminetetraacetate Complexes of Ruthenium(II) with Dinitrogen, Carbon Monoxide, and other π-Acceptor Ligands.

Urban et al, J. of Organometallic Chemistry 517, 1996, 191-200 Metal complexes of biologically important ligands, LXXXVII α-Amino carboxylate complexes of palladium(II), iridium(III) and ruthenium(II) from chlorobridged ortho-metallated metal compounds and $[(OC)_3Ru(Cl)(\mu-Cl)]_2$.

Motterlini et al, Carbon Monoxide-Releasing Molecules: Characterization Of Biomedical And Vascular Activities, Circulation Research. 2002, vol. 90, No. 2, 1-8.

Motterlini, R. et al.; "Characterization of vasoactive effects elicited by carbon monoxide-releasing molecules,"; Journal of Vascular Research, Abstracts, 8th International Symposium on Mechanisms of Vasodilation; May 31—Jun. 3, 2001; 055.

Durante W.; "Heme Oxygenase-1 in Growth Control and its Clinical Application to Vascular Disease"; J. Cell. Physiol.; 2003; 195; 373-82.

Gordeuk, V. P. et al; "Carbonyl Iron Therapy for Iron Deficiency Anemia"; Blood; 1986; 67(3); 745-752.

Huebers, H. A. et al.; "Absorption of carbonyl iron"; J. Lab. Clin. Med.; 1986; 108; 473-8.

Sacks, P. V. et al.; "Comparative bioavailability of elemental iron powders for repair of iron deficiency anemia in rats. Studies of efficacy and toxicity of carbonyl iron"; The American Journal of Clinical Nutrition, 1978; 31;566-73.

* cited by examiner

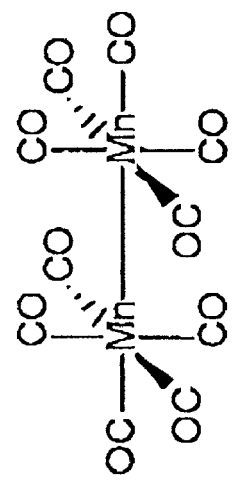
Dimanganese decacarbonyl [$Mn_2(CO)_{10}$]
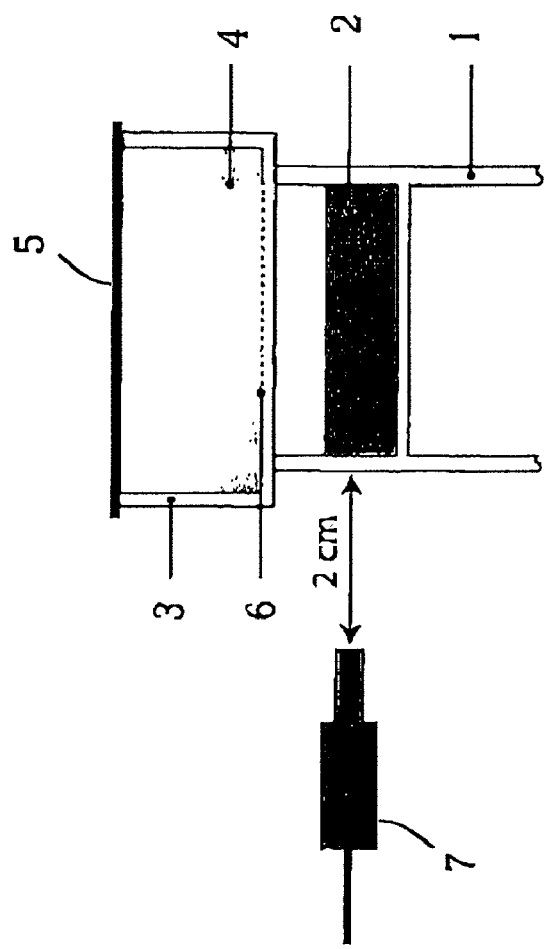
Fig. 1
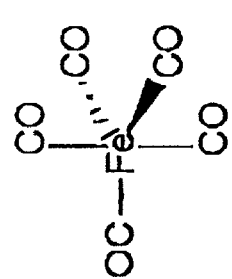
Iron pentacarbonyl [$Fe(CO)_5$]

Tricarbonyldichloro ruthenium(II) dimer
[Ru (CO)$_3$(Cl)$_2$]$_2$

| Compound | Structure | MW | CO Release (20 µmoles) | | | | CO Release (40 µmoles) | | | | NOTES |
|---|---|---|---|---|---|---|---|---|---|---|---|
| | | | 0 | 10 | 20 | 30 | 0 | 10 | 20 | 30 | |
| CO-RM-1 | [structure] | 512 | 12.0 ±3.0 | 16.3 ±4.0 | 18.1 ±4.3 | 18.5 ±4.8 | 28.5 ±0.4 | 32.0 ±0.2 | 34.5 ±0.5 | 35.6 ±0.4 | Soluble in DMSO |
| CO-RM-1a | [structure] | 384 | 7.2 ±0.6 | 8.6 ±0.3 | 8.0 ±0.4 | 7.5 ±0.4 | 16.9 ±0.6 | 18.4 ±0.3 | 17.3 ±0.3 | 16.7 ±0.2 | Soluble in DMSO |
| Negative control | [structure] | 484 | N.D. | N.D. | N.D. | N.D. | N.D. | N.D. | N.D. | N.D. | Soluble in H₂O |
| CO-RM-1b | [structure] | 334 | 6.4 ±1.2 | 7.3 ±0.6 | 8.2 ±0.1 | 8.7 ±0.3 | 11.7 ±0.8 | 13.7 ±0.9 | 14.0 ±1.1 | 14.4 ±0.6 | Soluble in DMSO |
| CO-RM-10 | [Ru(CO)₂Cl₂]ₙ | (228) | 2.6 ±0.6 | 9.8 ±0.3 | 12.7 ±0.1 | 13.8 ±0.9 | 8.6 ±0.7 | 21.0 ±1.1 | 24.4 ±1.0 | 26.3 ±1.2 | Soluble in DMSO |

Fig. 9(a)

| | | | | | | | | | | |
|---|---|---|---|---|---|---|---|---|---|---|
| CO-RM-11<br>Ligand: THF | 328 | 5.6<br>±0.6 | 5.9<br>±0.6 | 6.2<br>±1.1 | 6.2<br>±1.2 | 10.9<br>±0.2 | 12.3<br>±0.4 | 13.3<br>±0.4 | 13.7<br>±0.2 | Soluble in DMSO |
| CO-RM-16<br>Ligand: Cytidine | 742 | N.D. | 1.4<br>±0.4 | 2.1<br>±0.1 | 2.8<br>±0.4 | 0.8<br>±0.4 | 5.5<br>±0.4 | 8.4<br>±0.8 | 9.8<br>±0.9 | Soluble in $H_2O$ |
| CO-RM-17<br>Ligand: Guanosine | 539 | 5.9<br>±0.1 | 8.2<br>±0.4 | 8.5<br>±0.3 | 8.6<br>±0.4 | 11.5<br>±0.4 | 15.0<br>±0.4 | 15.6<br>±0.4 | 16.2<br>±0.3 | Soluble in $H_2O$ |

Fig. 9(b)

| | | | | | | | | | | |
|---|---|---|---|---|---|---|---|---|---|---|
| CO-RM-18<br>Ligand:<br>Guanosine | 822 | 10.1<br>±0.9 | 14.3<br>±0.4 | 14.1<br>±0.5 | 13.5<br>±0.4 | 25.4<br>±1.0 | 29.5<br>±1.5 | 29.5<br>±1.4 | 28.7<br>±1.3 | Soluble in<br>$H_2O$ |
| CO-RM-22<br>Ligand:<br>Guanine | 407 | 0.1<br>±0.1 | 0.8<br>±0.3 | 1.0<br>±0.3 | 2.3<br>±0.1 | 0.7<br>±0.1 | 1.9<br>±0.1 | 2.3<br>±0.1 | 2.4<br>±0.1 | Soluble in<br>$H_2O$<br>PPT |
| CO-RM-23<br>Ligand:<br>Guanine | 558 | 1.2<br>±0.1 | 1.3<br>±0.2 | 1.3<br>±0.1 | 1.0<br>±0.2 | 2.7<br>±0.3 | 2.7<br>±0.3 | 2.7<br>±0.4 | 2.3<br>±0.2 | Soluble in<br>$H_2O$<br>PPT |
| CO-RM-26<br>Ligand:<br>Cysteine | 340.5 | 0.6<br>±0.1 | 1.9<br>±0.1 | 2.3<br>±0.2 | 2.4<br>±0.2 | 1.9<br>±0.2 | 3.7<br>±0.1 | 5.1<br>±0.1 | 5.2<br>±0.1 | Soluble in<br>$H_2O$ |

Fig. 9(c)

| | | | | | | | | | |
|---|---|---|---|---|---|---|---|---|---|
| CO-RM-29<br>Ligand:<br>Triacetyle-<br>guanosine | 665 | 1.4<br>±0.7 | 4.5<br>±0.1 | 5.0<br>±0.1 | 3.2<br>±0.1 | 8.3<br>±0.6 | 11.7<br>±0.3 | 12.4<br>±0.1 | 10.6<br>±0.4 | Soluble in<br>H$_2$O |
| CO-RM-3<br>Ligand:<br>Glycine | 294.5 | 14.2<br>±0.6 | 17.8<br>±0.7 | 14.3<br>±0.7 | 12.9<br>±0.7 | 25.2<br>±1.5 | 24.4<br>±1.0 | 23.8<br>±0.6 | 23.2<br>±0.3 | Soluble in<br>H$_2$O |
| CO-RM-38<br>Ligand:<br>Isoleucine | 350.5 | 3.2<br>±0.2 | 4.4<br>±0.1 | 4.0<br>±0.2 | 3.0<br>±1.7 | 7.6<br>±1.3 | 8.3<br>±1.2 | 7.5<br>±1.1 | 7.3<br>±1.1 | Soluble in<br>H$_2$O |
| CO-RM-39<br>Ligand:<br>Serine | 324.5 | 11.0<br>±.03 | 12.8<br>±.09 | 11.4<br>±1.1 | 10.8<br>±.07 | 24.2<br>±1.5 | 24.6<br>±1.4 | 22.0<br>±1.0 | 21.9<br>±1.2 | Soluble in<br>H$_2$O |
| CO-RM-40<br>Ligand:<br>Alanine | 308.5 | 9.1<br>±1.1 | 11.9<br>±0.4 | 11.1<br>±.03 | 11.0<br>±0.2 | 20.2<br>±.06 | 21.3<br>±.09 | 19.9<br>±.09 | 19.6<br>±.09 | Soluble in<br>H$_2$O |

Fig. 9(d)

| | | | | | | | | | | |
|---|---|---|---|---|---|---|---|---|---|---|
| CO-RM-42 Ligand: Glutamine | [structure] | 365.5 | 8.9 ±0.4 | 11.1 ±0.4 | 12.1 ±1.4 | 10.1 ±0.3 | 21.4 ±2.1 | 21.8 ±2.2 | 20.6 ±2.0 | 20.0 ±1.8 | Soluble in H₂O |
| CO-RM-43 Ligand: Arginine | [structure] | 393.5 | 9.4 ±1.4 | 11.9 ±0.5 | 12.3 ±0.7 | 11.0 ±0.3 | 18.3 ±.03 | 20.0 ±0.6 | 19.0 ±1.2 | 17.8 ±1.3 | Soluble in H₂O |
| CO-RM-46 Ligand: Lysine | [structure] | 365.5 | 6.0 ±0.4 | 7.5 ±0.8 | 7.2 ±1.2 | 6.4 ±0.8 | 12.6 ±0.9 | 13.4 ±1.2 | 13.2 ±1.1 | 11.9 ±1.0 | Soluble in H₂O |
| CO-RM-57 Ligand: L-valine | [structure] | 336.5 | 11.1 ±2.9 | 18.2 ±1.7 | 17.6 ±1.6 | 17.0 ±1.6 | 29.3 ±1.5 | 34.6 ±2.2 | 33.7 ±2.2 | 32.8 ±2.2 | Soluble in H₂O |
| CO-RM-70 | [structure] | 240 | 0.5 ±0.2 | 0.9 ±0.1 | 2.2 ±0.2 | 2.7 ±0.3 | 0.9 ±0.1 | 2.0 ±0.2 | 4.9 ±0.2 | 6.3 ±0.3 | Soluble in DMSO PPT |
| CO-RM-71 | [structure] | 350 | 1.5 ±0.2 | 2.3 ±0.3 | 3.1 ±0.4 | 3.7 ±0.4 | 3.4 ±0.1 | 5.4 ±0.3 | 6.9 ±0.3 | 7.6 ±0.4 | Soluble in DMSO PPT |

Fig. 9(e)

| | | | | | | | | | | |
|---|---|---|---|---|---|---|---|---|---|---|
| CO-RM-74<br>Ligand:<br>L-Threonine | [structure] | 338.5 | 15.7<br>±1.2 | 17.5<br>±2.0 | 16.5<br>±2.3 | 14.8<br>±2.2 | 33.3<br>±0.2 | 33.4<br>±0.1 | 32.7<br>±0.2 | 31.4<br>±0.1 | Soluble in<br>$H_2O$ |
| CO-RM-97 | [structure] | 316 | 2.8<br>±0.6 | 7.0<br>±0.7 | 7.2<br>±0.9 | 6.6<br>±0.9 | 7.1<br>±0.5 | 14.3<br>±0.1 | 14.7<br>±0.8 | 13.6<br>±0.7 | Soluble in<br>$H_2O$ |
| CO-RM-99 | [structure] | 317 | 4.6<br>±0.6 | 8.1<br>±0.2 | 7.3<br>±0.3 | 5.5<br>±0.3 | 11.5<br>±0.2 | 16.6<br>±0.2 | 16.0<br>±0.9 | 14.0<br>±0.2 | Soluble in<br>$H_2O$ |
| CO-RM-H<br>Ligand:<br>L-proline | [structure] | 335 | 1.4<br>±0.3 | 4.7<br>±0.6 | 6.2<br>±0.8 | 6.3<br>±0.7 | 4.2<br>±0.4 | 9.9<br>±0.2 | 12.5<br>±0.1 | 13.0<br>±0.1 | Soluble in<br>$H_2O$ |

Fig. 9(f)

THERAPEUTIC DELIVERY OF CARBON MONOXIDE

FIELD OF THE INVENTION

The present invention relates to pharmaceutical compositions and compounds for the therapeutic delivery of carbon monoxide to humans and other mammals. Another use of the compositions and compounds is in organ perfusion.

BACKGROUND OF THE INVENTION

Carbon monoxide (CO) is, by common definition, a colorless, odorless, tasteless, non-corrosive gas of about the same density as that of air and is the most commonly encountered and pervasive poison in our environment. It is generally produced by the incomplete combustion of fossil fuels such as natural gas, propane, coal, gasoline and wood. In the atmosphere, the average global levels are estimated to be 0.19 parts per million (p.p.m.), 90% of which comes from natural sources including ocean micro-organism production, and 10% of which is generated by human activity Thus, inhalation of even small quantities of CO is inevitable for living organisms.

Depending on the extent and time of exposure, CO is capable of producing a myriad of debilitating and harmful residual effects to the organism (1). The most immediate of these effects, and perhaps the most notorious one, is binding to hemoglobin in the blood stream, which rapidly decreases the oxygen transport capability of the cardiovascular system. Paradoxically, more than half a century ago it was found that CO is constantly formed in humans in small quantities (2), and that under certain pathophysiological conditions this endogenous production of CO may be considerably increased (3–5). The discovery that hemoglobin, a heme-dependent protein, is required as substrate for the production of CO in vivo (6,7) and the identification of the enzyme heme oxygenase as the crucial pathway for the generation of this gaseous molecule in mammals (8) set the basis for the early investigation of an unexpected and still unrecognized role of CO in the vasculature (9). The succeeding cloning (10) and characterization of constitutive (HO-2) and inducible (HO-1) isoforms of heme oxygenase (11–13) as well as studies on the kinetics and tissue distribution of these enzymes (14) started to reveal a major importance of this pathway in the physiological degradation of heme. That is, the end products of heme degradation (CO, biliverdin and bilirubin) might possess, after all, crucial biological activities (15–17).

With regard to the cardiovascular system, the recognition that CO possesses vasodilatory properties (18–20) is, perhaps, the most significant evidence in favor of a pharmacological function of CO. Although the molecular mechanisms and the chemical modifications that are required to transduce the signals mediated by CO into a specific biological effect need to be fully elucidated, convincing scientific reports have recently highlighted the signaling properties of endogenously generated CO (21–24).

Experimental studies on the physiological effects of nitric oxide (NO) have been facilitated by the development of a wide variety of organic compounds that spontaneously release NO and can be easily acquired to reproduce a physiological or pathophysiological function of NO. There is now abundant literature on the different types of NO donors and NO-releasing agents that, depending on their stability and half-life, can be used in disparate in vitro and in vivo models to simulate the biological activity of this important signaling molecule (25,26). In clinical practice, compounds that deliver No into the circulation such as sodium nitroprusside and glyceryl trinitrate are used to lower blood pressure and treat certain cardiovascular diseases (27). Drugs containing a functional NO group that can selectively target an organ or tissue are currently being developed or are under clinical trials for the treatment of specific pathophysiological states (28,29). However, to date no compounds capable of delivering CO therapeutically have been identified.

U.S. Pat. No. 5,882,674 proposes administration of CO via transdermal delivery systems containing metal carbonyl complexes such as iron pentacarbonyl and iron enneacarbonyl. However, since this document provides no experimental data, and no description of specific devices, it is not clear how this proposal can be made to work. In particular it is not stated whether the iron carbonyl complex is intended to be absorbed from the patch, to release CO within the body, or whether the complex breaks down within the patch to release CO which then enters the bloodstream after absorption through the skin. If, and to the extent that, this document is considered to make available pharmaceutical devices, compositions and methods for the practical and effective delivery of carbon monoxide in viva, such devices, compositions and methods are excluded from the scope of the present invention.

Amongst literature relating to metal carbonyls, WO98/48848 describes facial metal tricarbonyl compounds and their use in the labelling of biologically active substrates The metals, preferably radionuclides, are of Group 7, the metals identified being Mn, $^{99m}$Tc, $^{186}$Re and $^{188}$Re. The compounds fac-$[M(CO)_3(OH_2)_3]^+$ where M is the metal are proposed for labelling of biologically active substrates, as a result of which metal carbonyl compounds having a variety of biologically active ligands are obtained. In the examples radioactive Tc is used. The document describes preparation of diagnostic and therapeutic compositions but no therapeutic composition is specifically disclosed, nor is any treatment of any condition by therapy mentioned. There is no disclosure of use of the compounds for delivering carbon monoxide to physiological targets. If, and to the extent that, this document is regarded as disclosing a therapeutic use or mode of therapeutic administration of the carbonyl compounds, that subject matter is excluded from the scope of the present invention. Preferably the present invention excludes use of the facial carbonyl compounds disclosed in this document in any event.

WO 91/01128 and WO 91/01301 describe compositions for treating skin to repair the effects of photoaging by topical application or to treat acne or psoriasis by topical or oral administration. The active compounds are polyene esters and iron carbonyl complexes thereof. Specifically the iron of iron tri-carbonyl is coordinated to the polyene chain. No reason for including the iron carbonyl is mentioned. Insofar as therapeutic uses or compositions of carbonyl compounds are disclosed in these two documents, such uses and compositions are specifically excluded from the scope of the present invention.

WO 98/29115 describes compositions and methods for relaxing smooth muscle in a warm-blooded animal by administering certain transition metal nitrosyl compounds. Treatments of hypertension, angina pectoris, congestive heart failure and impotence are mentioned. Some of the compounds contain, in addition to NO, CO as a ligand. Specifically the CO-containing compound has the formula $L_3M(NO)_yX_{3-y}$ where L is a two-electron Lewis base or $L_3$ is a six-electron Lewis base, M is a Group 6 or 8 transition metal and when y is 1, X is carbon monoxide. The essential teaching of this document is concerned with the therapeutic effect of nitrosyl complexes. There is no disclosure that the CO ligand, when present, has any therapeutic effect by delivery of CO to a physiological target. The CO-containing metal nitrosyl complexes disclosed in it are excluded from the novel metal carbonyls of the present invention and their uses for treatments mentioned are also excluded from the present invention. Preferably transition metal nitrosyl complexes containing CO are excluded from the scope of the present invention in any event.

HU-B-211084 describes a composition, which is for oral administration, for the fortification of bones containing calcium phosphate, at least one calcium salt of an organic acid and optionally iron pentacarbonyl The present invention does not extend to the use of iron pentacarbonyl in combination with calcium compounds as specified in this document in connection with the therapeutic uses and modes of administration described there, and preferably does not extend to the use of iron carbonyls and complexes including iron and CO in combination with calcium phosphates and/or calcium salts of organic acids in any event.

WO 95/05814 (U.S. Pat. No. 6,284,752) and WO 00/56743 both disclose a very wide range of metal complexes, for use in treatment of disease relating to the overproduction of reactive oxygen species, particularly overproduction of NO. The stated aim is to modulate NO levels in the body by scavenging, or removing, NO in situ. The ex-vivo test data are stated to show that vasoconstriction is a direct result of the removal of endogenous nitric oxide. Carbon monoxide is mentioned as a possible ligand, but no example of a complex containing carbon monoxide is given and no effect is attributed to CO. Insofar as these documents are considered to disclose practical use of a complex containing CO for the specified purpose, such use does not form part of the present invention.

SUMMARY OF THE INVENTION

As exemplified by the experimental data detailed below, the present inventors have found that metal carbonyl compounds can be used to deliver CO to a physiological target so as to provide physiological effect.

Accordingly the present invention provides a pharmaceutical composition, for delivery of carbon monoxide to a physiological target, comprising a metal carbonyl compound or pharmaceutically acceptable salt thereof and at least one pharmaceutically acceptable carrier, wherein the metal carbonyl makes available CO suitable for physiological effect by at least one of the following means:

1) CO derived by dissociation of the metal carbonyl is present in the composition in dissolved form;
2) on contact with a solvent the metal carbonyl releases CO;
3) on contact with a tissue, organ or cell the metal carbonyl releases CO;
4) on irradiation the metal carbonyl releases CO.

Certain metal carbonyl compounds are capable of releasing CO on contact with a suitable solvent. When the pharmaceutical composition is to be administered in liquid form, this solvent may form a component part of the pharmaceutical composition. Thus in this aspect of the invention, the pharmaceutical composition contains CO derived from the metal carbonyl in dissolved form. The conditions under which the carbonyl compound is dissolved in the solvent during preparation of the pharmaceutical may be controlled such that the CO thus released is retained in solution. This may be facilitated where an equilibrium exists between the dissociated components and the undissociated carbonyl.

The dissociated components of the parent carbonyl may themselves be metal carbonyl complexes capable of releasing further CO. For example, when $[Ru(CO)_3Cl_2]_2$ is dissolved in DMSO, CO is liberated into solution, and a mixture of tri-carbonyl and di-carbonyl complexes is formed, and these themselves may be capable of releasing further CO.

In a further aspect of the invention, the pharmaceutical composition may not itself contain dissolved CO, but may be prepared such as to release CO on contact with a suitable solvent or medium. For example, the composition may contain a metal carbonyl compound capable of releasing CO on contact with water, e.g. on contact with an aqueous physiological fluid, such as blood or lymph. Alternatively, the pharmaceutical composition may be intended to be dissolved in water prior to administration. Such pharmaceutical compositions may be prepared in solution or in solid form, such as in tablet form. If they are in solution form, they will typically be prepared in a solvent which does not support dissociation of the metal carbonyl compound, such that release of CO takes place only on contact with the appropriate solvent.

Alternatively or additionally, release of CO from the complex can be stimulated by reaction with a ligand in solution which for example replaces one of the ligands of the complex leading to loss of CO from the complex.

In another aspect of the invention the pharmaceutical composition may contain a metal carbonyl compound which releases CO on contact with a tissue, organ or cell. It is shown below that certain metal carbonyl compounds do not release CO to solution but are nevertheless capable of releasing CO to physiological cellular materials or tissues, such as vascular endothelium. For example, $[Fe(SPh)_2(2,2'-bipyridine)(CO)_2]$ is shown below not to release CO to myoglobin in solution, but is nevertheless capable of promoting dilatation of pre-contracted aortic rings. Without wishing to be limited by any particular theory, it is thought that CO may be released from such compounds as a result of an oxidation-reduction reaction, mediated by cellular components such as cytochromes.

However the invention is not limited to a redox reaction as a mechanism for CO release, since loss of at least a first CO from the complex may occur without redox.

In a further aspect of the invention, the pharmaceutical composition may contain a metal carbonyl compound which releases CO on irradiation. The compound may be irradiated prior to administration, for example to produce a solution of dissolved CO, or may be irradiated in situ after administration. It is contemplated that such compositions may be used to provide controlled, localised release of CO. For example a pharmaceutical composition of this type may be administered during surgery, and CO released specifically at a site in need thereof, e.g. to induce vasodilation, by localised irradiation by means of a laser or other radiant energy source, such as UV rays.

Typically the pharmaceutical compositions of the present invention release CO such as to make it available to a therapeutic target in dissolved form. However, in some circumstances CO may be released from a metal carbonyl directly to a non-solvent acceptor molecule.

It will be apparent that pharmaceutical compositions according to the present invention may be capable of delivering CO therapeutically through one or more of the above described modes of action.

Typically the metal carbonyl compound comprises a complex of a transition metal, preferably a transition metal from group 7 or groups 8 to 10 (in this specification the groups of the periodic table are numbered according to the IUPAC system from 1 to 18). The number of carbonyl ligands is not limited, provided at least one carbonyl ligand is present. The preferred metals are transition metals of lower molecular weight, in particular Fe, Ru, Mn, Co, Ni, Mo and Rh. Two other metals which may be used are Pd and Pt. In the metal carbonyl complexes used in the invention, the metal is typically in a low oxidation state, i.e. O, I or II. For the metals preferred, the oxidation states are typically not higher than $Fe^{II}$, $Ru^{II}$, $Mn^{I}$, $Co^{II}$ preferably $Co^{I}$, $Rh^{III}$ preferably $Rh^{I}$, $Ni^{II}$, $Mo^{II}$. The metal is preferably not a radionuclide. Fe is one particularly suitable metal, since Fe is present in quantity in mammals.

The metal carbonyl compounds may be regarded as complexes, because they comprise CO groups coordinated to a metal centre. However the metal may be bonded to other groups by other than coordination bonds, e.g. by ionic or covalent bonds. Thus groups other than CO which form part of the metal carbonyl compound need not strictly be "ligands" in the sense of being coordinated to a metal centre via a lone electron pair, but will be referred to herein as "ligands" for ease of reference.

Thus, the ligands to the metal may all be carbonyl ligands, as e.g. in $[Mn_2(CO)_{10}]$. Alternatively, the carbonyl compound may comprise at least one modulatory ligand. By this is meant a ligand which is not CO, but which modulates a particular property of the complex, such as the tendency to release CO, solubility, hydrophobicity, stability, electrochemical potential, etc. Thus suitable choices of ligand may be made in order to modulate the behaviour of the compound. For example it may be desirable to modulate the solubility of the compound in organic and/or aqueous solvents, its ability to cross cell membranes, its rate of release of CO on contact with a particular solvent or cell type, or on irradiation, etc.

Such ligands are typically neutral or anionic ligands, such as halide, or derived from Lewis bases and having N, P, O or S or a conjugated carbon group as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as $NEt_3$ and $H_2NCH_2CH_2NH_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as $Et_2O$ and tetrahydrofuran, alcohols such as EtOH, and nitrites such as MeCN. Particularly preferred are coordinating ligands, such as amino acids, which render the carbonyl complex stable in aqueous solution. Other possible ligands are conjugated carbon groups, such as dienes. One class of ligands which can provide metal carbonyl compounds of use in this invention is cyclopentadiene ($C_5H_5$) and substituted cyclopentadiene. The substituent group in substituted cyclopentadiene may be for example an alkanol, an ether or an ester, e.g. $-(CH_2)_nOH$ where n is 1 to 4, particularly $-CH_2OH$, $-(CH_2)_nOR$ where n is 1 to 4 and R is hydrocarbon preferably alkyl of 1 to 4 carbon atoms and $-(CH_2)_nOOCR$ where n is 1 to 4 and R is hydrocarbon preferably alkyl of 1 to 4 carbon atoms. The preferred metal in such a cyclopentadiene or substituted cyclopentadiene carbonyl complex is Fe. Preferably the cyclopentadiene carbonyl complex is cationic, being associated with an anion such as chloride.

As mentioned above certain metal nitrosyl complexes disclosed in WO 98/29115 and their uses disclosed are excluded from the present invention, and preferably the invention does not extend to metal carbonyl complexes containing NO (nitrosyl) in any event. Furthermore as mentioned above certain iron carbonyl complexes disclosed in WO 91/01128 and WO 91/01301 and their uses disclosed therein are excluded from the present invention. Preferably the invention does not extend to topical or oral administration of iron carbonyl polyene complexes, nor to these complexes in themselves.

A further exclusion from the present invention are the Mn and radionuclide complexes disclosed in WO 98/48848. Preferably the present invention excludes therapeutic use of these Mn complexes. Preferably the invention excludes carbonyls of radioactive metals, in any case.

CO is suggested to act at least in part through the stimulation of guanylate cyclase activity. Thus the metal carbonyl compound may desirably comprise ligands which modulate the effect of CO on guanylate cyclase. For example, the drug YC-1 (3-(5'-hydroxymethyl-2'-furyl)-1-benzylindole) is thought to enhance stimulation of guanylate cyclase by CO. Thus incorporation of ligands such as YC-1 or derivatives thereof into the metal carbonyl compounds can alter or enhance the biological effects of the released CO.

Thus the properties of pharmaceutical compositions of the present invention may be tailored as required by appropriate choice of metal centres and number and type of associated ligands in the metal carbonyl compound.

The metal carbonyl compound may further comprise a targeting moiety, to facilitate release of CO at an appropriate site. The targeting moiety is typically capable of binding a receptor on a particular target cell surface, in order to promote release of CO at the required site. The targeting moiety may be a part of a modulating ligand capable of binding to a receptor found on the surface of the target cells, or may be derived from another molecule, such as an antibody directed against a particular receptor, joined to the complex by a suitable linker.

The present invention also provides a pharmaceutical composition for delivery of CO, comprising as active ingredient a compound of the formula $M(CO)_xA_y$ where x is at least one, y is at least one, M is a metal, A is an atom or group bonded to M by an ionic, covalent or coordination bond, and, in the case where y>1, each A may be the same or different, or a pharmaceutically acceptable salt of such a compound. Typically, M is a transition metal, particularly of group 7 or groups 8 to 10, and A may be selected from halogens, groups having N, P, O or S atoms providing lone electron pairs for coordination bonding to M, and conjugated carbon groups. More details of preferred metals and ligands are given above. The carbonyl complex should be pharmaceutically acceptable, in particular non-toxic or of acceptable toxicity at the dosage levels envisaged.

The pharmaceutical compositions of the present invention typically comprise a pharmaceutically acceptable excipient, carrier, buffer, stabiliser or other materials well known to those skilled in the art. Such materials should be non-toxic and should not interfere unduly with the efficacy of the active ingredient. The precise nature of the carrier or other material may depend on the route of administration, e.g. oral, intravenous, subcutaneous, nasal, intramuscular, intraperitoneal, or suppository routes.

Pharmaceutical compositions for oral administration may be in tablet, capsule, powder or liquid form. A tablet may include a solid carrier such as gelatin or an adjuvant or a slow-release polymer. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, in particular where they are required for dissolving the particular metal carbonyl compound contained in the composition.

For intravenous, cutaneous or subcutaneous injection, or injection at the site of affliction, the active ingredient will typically be in the form of a parenterally acceptable solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Delivery systems for needle-free infection are also known, and compositions for use with such systems may be prepared accordingly.

Administration is preferably in a prophylactically effective amount or a therapeutically effective amount (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

When formulating pharmaceutical compositions according to the present invention, the toxicity of the active ingredient and/or the solvent must be considered. The balance between medical benefit and toxicity should be taken into account. The dosages and formulations of the compositions will typically be determined so that the medical benefit provided outweighs any risks due to the toxicity of the constituents.

There is further provided a method of introducing CO to a mammal comprising the step of administering a pharmaceutical composition according to the present invention. CO is thought to act at least in part through stimulation or activation of guanylate cyclase. CO is thought to have functions as, inter alia, a neurotransmitter and a vasodilating agent. Accordingly there is provided a method of delivering CO to a mammal for stimulation of guanylate cyclase activity. There is further provided a method of delivering CO to a mammal for stimulating neurotransmission or vasodilation. However the present applicants do not wish to be bound by theory and do not exclude the possibility that CO operates by other mechanisms.

The heme oxygenase 1 (HO-1) pathway is thought to represent a pivotal endogenous inducible defensive system against stressful stimuli including UVA radiations, carcinogens, ischaemia-reperfusion damage, endotoxic shock and several other conditions characterised by production of oxygen free radicals (30–32). The protective effect of HO-1 is attributed to the generation of the powerful antioxidants biliverdin and bilirubin and the vasoactive gas CO. Expression of HO-1 has been linked with cardiac xenograft survival (33), suppression of transplant arteriosclerosis (34) and amelioration of post-ischemic myocardial dysfunction (35). HO-1 has also been directly implicated in the resolution phase of acute inflammation in rats (36). Other pathological situations, such as haemorrhagic shock in brain and liver as well as sepsis (37–39), are characterized by induction of the HO-1 gene, which seems to play a crucial role in counteracting the vascular dysfunction caused by these pathophysiological states. Increased generation of CO as a consequence of HO-1 induction markedly affects vessel contractility and diminishes acute hypertension in the whole organism (23, 40). Exposure of animals to ambient air containing low concentrations of CO or transfection of the HO-1 gene results in protection against hyperoxia-induced lung injury in vivo, a mechanism mediated by attenuation of both neutrophil inflammation and lung apoptosis (cell death) (41,42). Exogenous CO gas also has the ability to suppress pro-inflammatory cytokines and modulate the expression of the anti-inflammatory molecule, IL-10, both in vitro and in vivo (43). Therefore administration of CO in accordance with the invention may be used for treatment of any of these conditions, for modulation of inflammatory states and regression of other pathophysiological conditions including cancer.

Accordingly there is provided a method of introducing CO to a mammal comprising the step of administering a pharmaceutical composition according to the present invention, for treatment of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

The present invention also provides the use of a metal carbonyl compound as herein described in the manufacture of a medicament for delivering CO to a physiological target, particularly a mammal, to provide a physiological effect, e.g. for stimulating neurotransmission or vasodilation, or for treatment of any of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome. Such medicaments may be adapted for administration by an oral, intravenous, subcutaneous, nasal, inhalatory, intramuscular, intraperitoneal or suppository route. Preferably the present invention excludes delivery of a metal carbonyl or a decomposition product thereof to an organism through the skin or mucosa.

The invention further provides use of the metal carbonyls here described in treatment, e.g. by perfusion, of a viable mammalian organ extracorporeally, e.g. during storage and/or transport of an organ for transplant surgery. For this purpose, the metal carbonyl is in dissolved form, preferably in an aqueous solution. The viable organ may be any tissue containing living cells, such as a heart, a kidney, a liver, a skin or muscle flap, etc.

The invention also consists in a metal carbonyl compound of the formula $M(CO)_xA_yB_z$ where M is Fe, Co or Ru,
x is at least one,
y is at least one,
z is zero or at least one,
each A is a ligand other than CO and is monodentate or polydentate with respect to M and is selected from the amino acids
  alanine
  arginine
  asparagine
  aspartic acid
  cysteine
  glutamic acid
  glutamine
  glycine
  histidine
  isoleucine
  leucine
  lysine
  methionine
  phenylalanine
  proline
  serine
  threonine
  tryptophan
  tyrosine
  valine $O(CH_2COO)_2$ and $NH(CH_2COO)_2$, and B is optional and is a ligand other than CO, excluding $Fe(CO)_x A_y$ where A is cysteine or an ester of cysteine and $Ru(CO)_xA_y$ where A is proline.

x is preferably 3, y is preferably 1 and z is preferably 1.

The term amino acid here used includes the species obtained by loss of the acidic hydrogen, such as glycinato.

$B_z$ represents one or more optional other ligands. There are no particular limitations on B, and ligands such as halides, e.g. chloride, bromide, iodide, and carboxylates, e.g. acetate may be used.

M is selected from Fe, Ru and Co. These metals are preferably in low oxidation states, as described above.

Use of the known iron compounds [Fe(SPh)$_2$(2,2'-bipyridine)(CO)$_2$] and [Fe(SPh)$_2$(NH$_2$CH$_2$CH$_2$NH$_2$)(CO)$_2$] is also envisaged in this invention.

It is further considered that, in place of the metal carbonyl compounds discussed above, the pharmaceutical compositions of the present invention may comprise oxalate compounds, formic acid, or formate compounds, which may likewise deliver CO to a physiological target. For example, bis-(2,4-dinitrophenyl) oxalate is known to decompose in water to liberate CO into solution. Therefore the present invention further provides a pharmaceutical composition, for delivery of carbon monoxide to a physiological target, comprising formic acid, a formate, a formate ester or amide, an oxalate, or an oxalate ester or amide, or a pharmaceutically acceptable salt thereof and at least one pharmaceutically acceptable carrier, wherein the formic acid, formate or oxalate or amide or ester makes available CO suitable for physiological effect.

It is thought that the nitrophenyl groups of bis-(2,4-dinitrophenyl) oxalate are good leaving groups, because of the electron-withdrawing effects of the nitro groups, and that this may promote the decomposition of the oxalate to yield CO.

It is therefore considered that oxalates or formates having in which the acid groups are linked, e.g. by an ester bond, to aromatic groups with electron-withdrawing substituents, such as tosyl groups, are particularly suitable for use in pharmaceutical compositions according to the present invention.

There is further provided a method of introducing carbon monoxide to a mammal comprising the step of administering a pharmaceutical composition comprising formic acid, a formate, a formate ester or amide or an oxalate, an oxalate ester or amide, or a pharmaceutically acceptable salt thereof, and at least one pharmaceutically acceptable carrier.

All the above discussion and disclosure relating to metal carbonyl compounds is also considered to relate to formic acid, formates, oxalates and formate or oxalate amides and esters.

Throughout this application, references to medical treatment are intended to include both human and veterinary treatment, and references to pharmaceutical compositions are accordingly intended to encompass compositions for use in human or veterinary treatment.

INTRODUCTION OF THE DRAWINGS

Experimental data illustrating the present invention will now be described by reference to the accompanying figures, in which:

FIG. 1 shows apparatus for measuring release of CO by metal carbonyl complexes on irradiation and structures of [Mn$_2$(CO)$_{10}$] and [Fe(CO)$_5$].

FIGS. 9*a* to 9*f* are tables presenting CO release data of metal carbonyl complexes.

Figure 10:
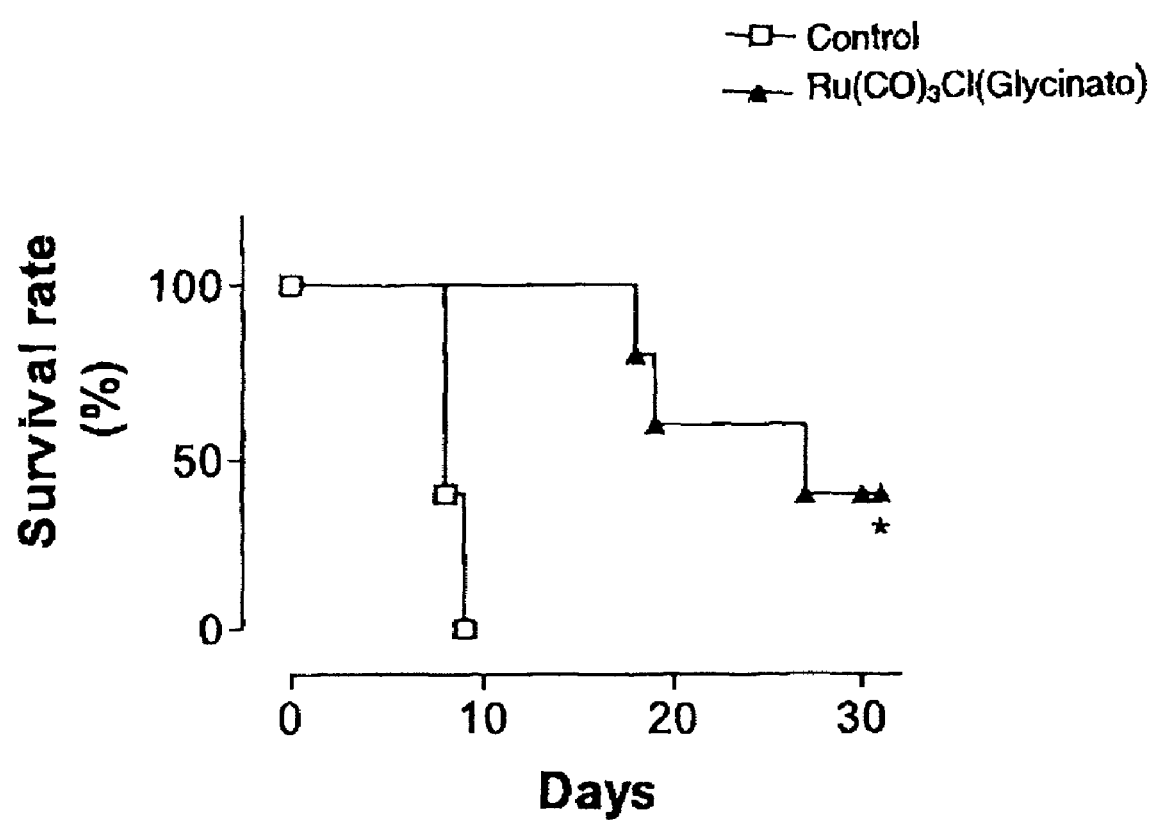

FIG. 10 is a graph showing survival rates in a transplant rejection study described below.

Figure 11:
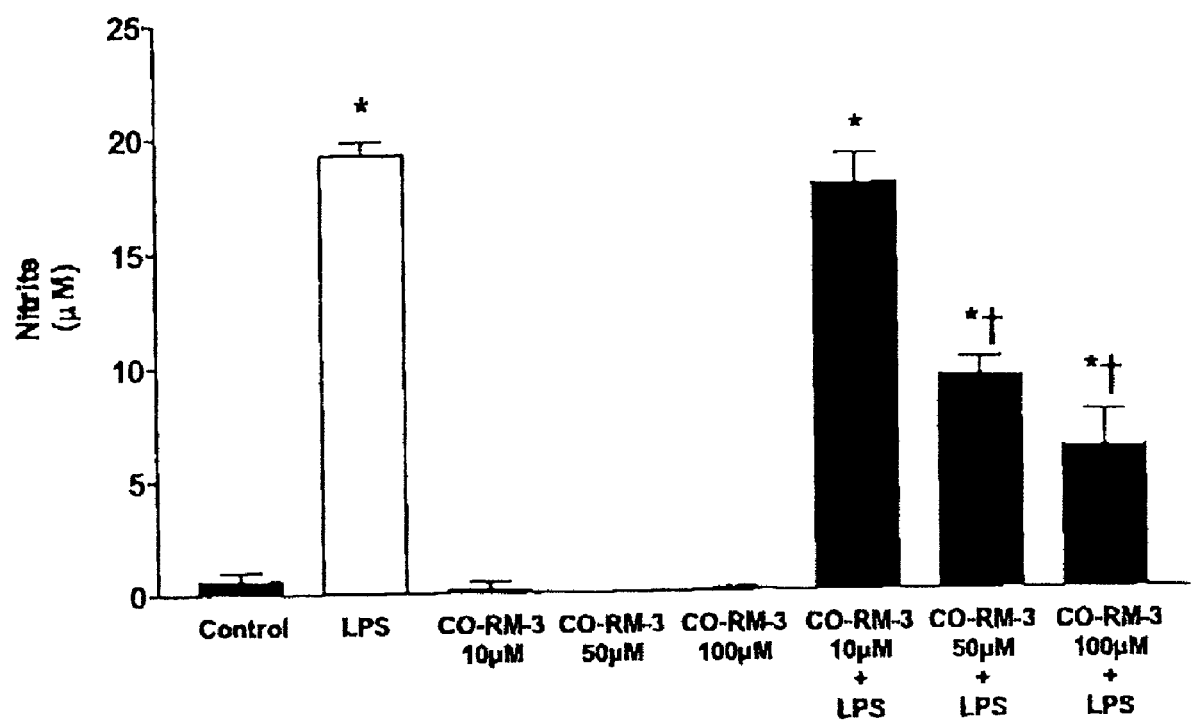

FIG. 11 is a graph of nitrite produced in a study of NO production in macrophages described below.

Figure 12:
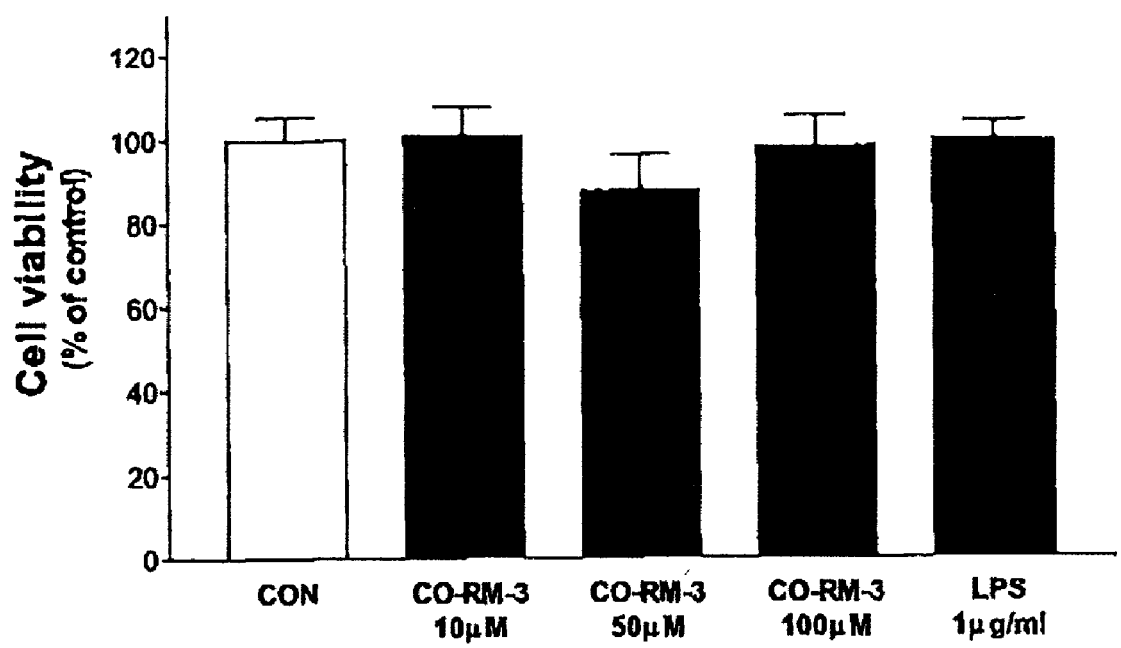
Figure 12:
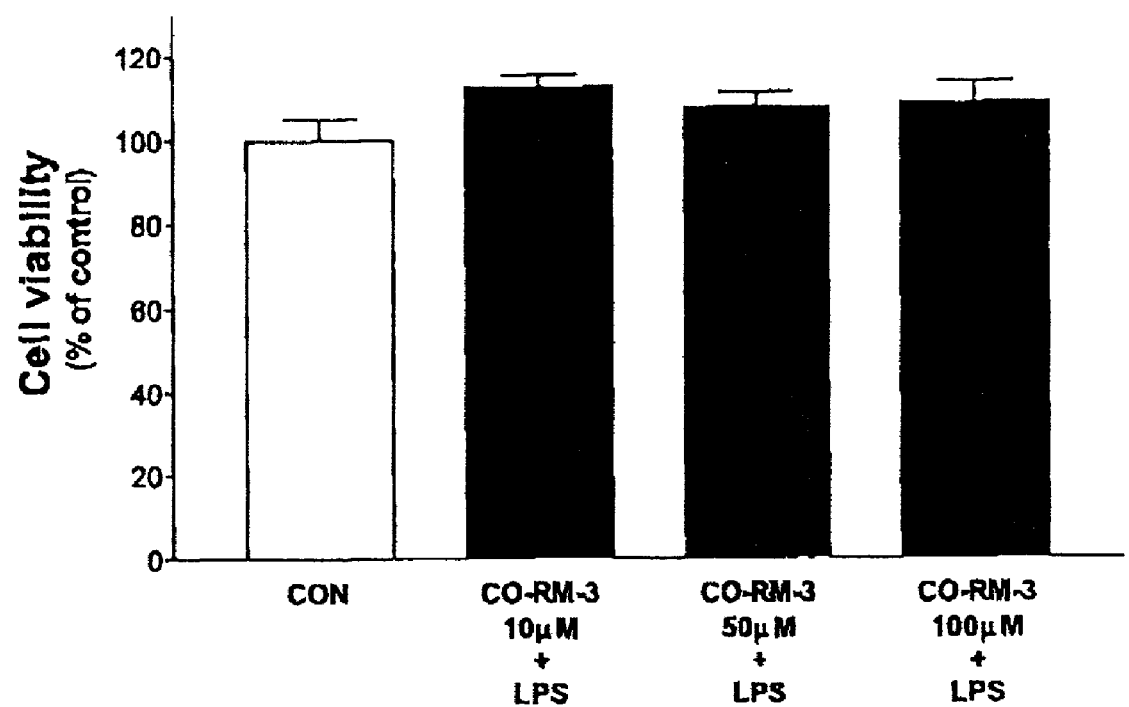

FIG. 12 is graphs of cell viability in the study of NO production in macrophages.

EMBODIMENTS OF THE INVENTION AND EXPERIMENTAL DATA

For the experiments here described, iron pentacarbonyl, [Fe(CO)$_5$], dimanganese decacarbonyl, [Mn$_2$(CO)$_{10}$], tricarbonyldichlororuthenium (II) dimer, [Ru(CO)$_3$Cl$_2$]$_2$, and ruthenium(III) chloride hydrate, RuCl$_3$, were purchased from Sigma-Aldrich Company Ltd. (Poole, Dorset, UK). Other carbonyl complexes have been synthesized, as described below. Stock solutions of metal carbonyl complexes were prepared fresh prior to each experiment by dissolving the compounds in dimethyl sulfoxide (DMSO), water or saline. Hemin (ferriprotoporphyrin IX chloride) and tin protoporphyrin IX (SnPPIX) were from Porphyrin Products Inc. (Logan, Utah, USA). Stock solutions of both porphyrins were prepared by dissolving the compounds in 0.1 M NaOH and then adjusting the pH to 7.4 by addition of 0.01 M phosphate buffer. The guanylate cyclase inhibitor, [1H-[1,2,4]Oxadiazole[4,3-a]quinoxalin-1-one] (ODQ), was obtained from Alexis Corporation (Bingham, Nottingham, UK) and polyclonal rabbit anti-HO-1 antibodies were purchased from Stressgen (Victoria, Canada). Horse heart myoglobin, $N^G$-nitro-L-arginine methyl ester (L-NAME) and all other reagents were from Sigma, unless otherwise specified All data are expressed as mean±s.e.m. Differences between the groups analysed were assessed by the Student's two-tailed t-test, and an analysis of variance (ANOVA) was performed where more than two treatments were compared. Results were considered statistically significant at $P<0.05$.

A. Detection of CO Liberated from Transition Metal Carbonyl Complexes.

The release of CO from metal carbonyl complexes was assessed spectrophotometrically by measuring the conversion of deoxymyoglobin (deoxy-Mb) to carbonmonoxy myoglobin (MbCO). MbCO has a distinctive absorption spectrum between 500 and 600 nm, and changes at 540 nm were used to quantify the amount of CO liberated. Myoglobin solutions (66 µM final concentration) were prepared freshly by dissolving the protein in 0.04 M phosphate buffer (pH 6.8). Sodium dithionite (0.1%) was added to convert myoglobin to deoxy-Mb prior to each reading. All the spectra were measured using a Helios α spectrophotometer.

Direct addition of iron pentacarbonyl, $[Fe(CO)_5]$, or dimanganese decacarbonyl, $[Mn_2(CO)_{10}]$, to myoglobin solutions did not result in any appreciable formation of carbonmonoxy myoglobin (MbCO) over time (data not shown). This is consistent with the notion that these two transition metal carbonyl complexes do not release CO unless stimulated by light (44,45). Therefore release of CO was induced by exposing these metal carbonyl complexes to a cold light source and allowing the gas to diffuse through a membrane before reacting with myoglobin as shown in FIG. 1.

Five hundred microliters of iron pentacarbonyl ($[Fe(CO)^15]$, 99.9%) or 1 ml of dimanganese decacarbonyl ($[Mn_2(CO)_{10})$, 13 mM in DMSO) (see also chemical structure) were placed as carbonyl solution 2 in a plastic tube 1. A cell culture insert 3 (Costar) was sealed on top in order to create two separate chambers with a 0.6 cm air space between the solution 2 and an insert membrane 6 (Anapore™ 0.4 µm). 1.5 ml of deoxy-Mb solution (66 µM) was placed in the insert which was covered with Parafilm™ 5. The carbonyl solution was then exposed to cold light from a source 7 to stimulate CO release, allowing the gas to diffuse through the membrane 6 into the myoglobin solution 4. Aliquots of the myoglobin solution 4 were taken at different times and the conversion of deoxy-Mb to MbCO measured spectrophotometrically.

Figures 2A, 2B, 2C, 2D:
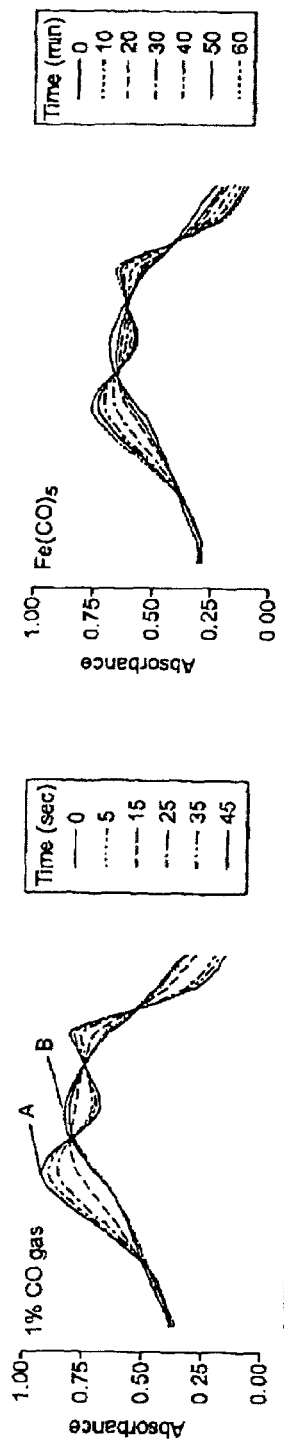
FIG. 2 shows deoxy-myoglobin and CO-myoglobin absorption spectra.

The spectral change on transition from deoxy-Mb to MbCO was measured by bubbling CO gas to a solution of deoxy-Mb (FIG. 2a). Upon illumination, $[Fe(CO)_5]$ and $(Mn_2(CO)_{10}]$ produced a similar change in the absorbance spectrum of myoglobin, with a gradual increase in MbCO formation observed over time; in both cases the distinctive identified spectra were the ones typical of MbCO (FIGS. 2b and 2c). Under the experimental conditions used, a complete saturation of the myoglobin solution was achieved by $[Mn_2(CO)_{10}]$ (13 µmol/ml) in approximately 40 min of continuous exposure to light (FIG. 2d).

Various metal carbonyl complexes were tested for their ability to elicit MbCO formation when added directly to a deoxy-Mb solution. To different extents, $[Ru(CO)_3Cl_2]_2$, $[Ru(CO)_2(DMSO)_2Cl_2]$, $[Ru(CO)_3Cl_2(cytosine)]$ and $[Ru(CO)_3(glycinate)Cl]$ all released CO when added directly to the Mb solution. No MbCO was detected in the case of $[Fe(SPh)_2(2,2'-bipyridine)(CO)_2]$ and $[Fe(SPh)_2(H_2NCH_2CH_2NH_2)(CO)_2]$, but as shown below both these compounds provided a vasodilatory effect.

Figure 2E:
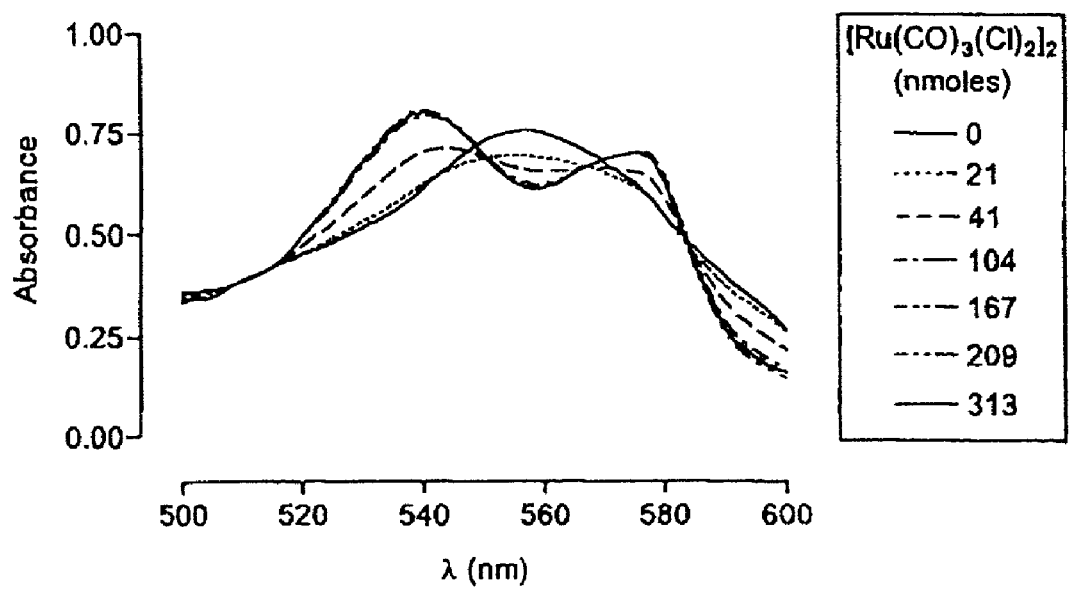
Figure 2F:
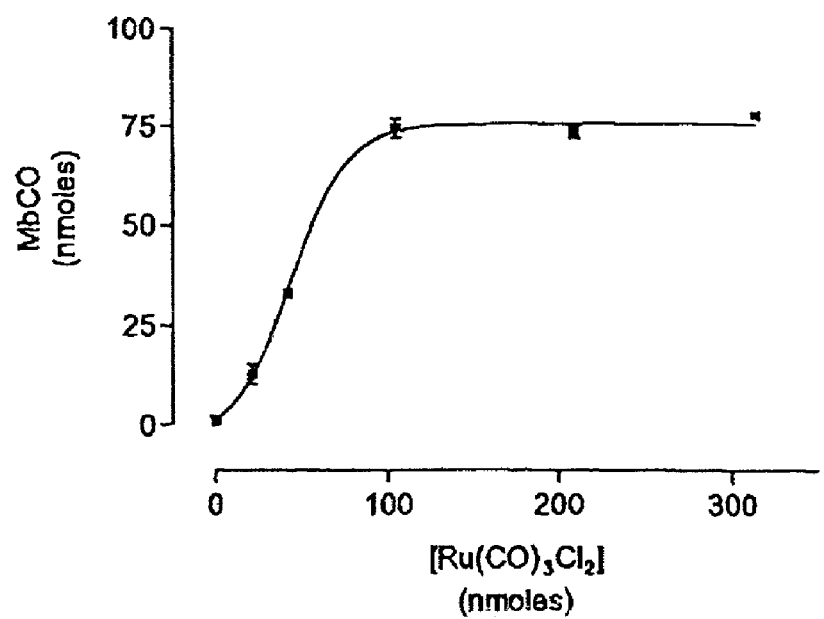

Data for the tricarbonyldichlororuthenium (II) dimer $[Ru(CO)_3Cl_2]_2$ are shown in FIG. 2e. The metal carbonyl complex was solubilized in DMSO (9.7 mM stock solution), aliquots of 2 to 32 µl were added directly to 1 ml of deoxy-Mb solutions (66 µM) and absorption spectrum determined immediately after mixing the samples by inversion. A linear regression analysis of the saturation curve of MbCO revealed that for each mole of $[Ru(CO)_3Cl_2]_2$ approximately 0.7 moles of CO are liberated (FIG. 2f).

Further data on release of CO measured by the same test procedure is described in section H below.

B. NMR Studies of $[Ru(CO)_3Cl_2]_2$

Figure 3:
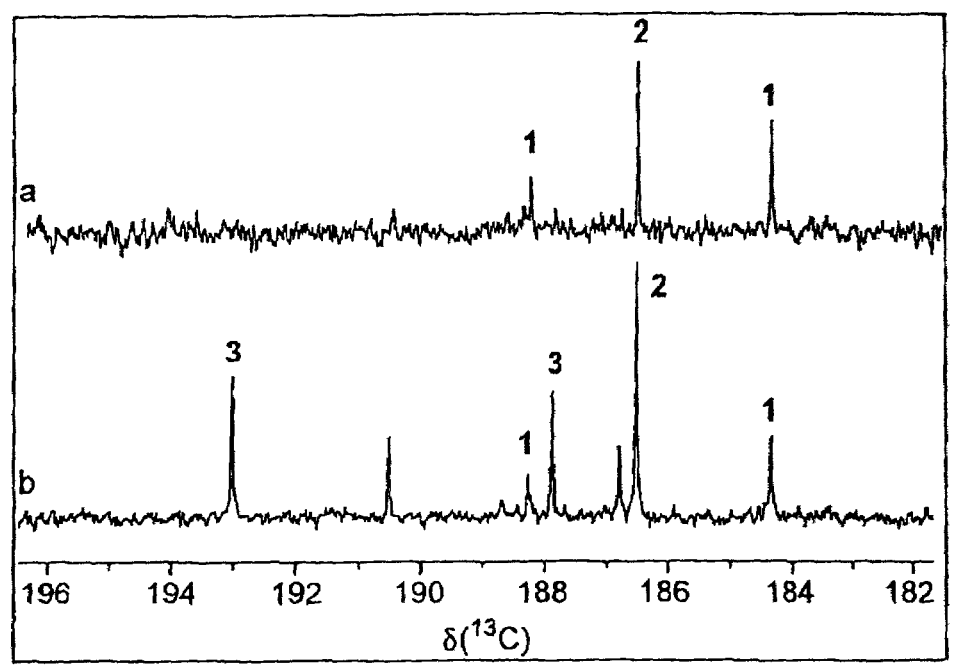
FIG. 3 shows NMR spectra illustrating the dissolution of [Ru(CO)$_3$Cl$_2$]$_2$ in DMSO.
Figure 3:
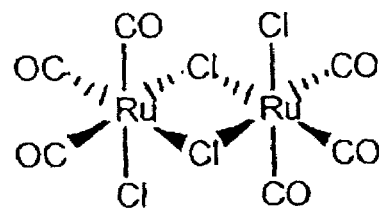
Figure 3:
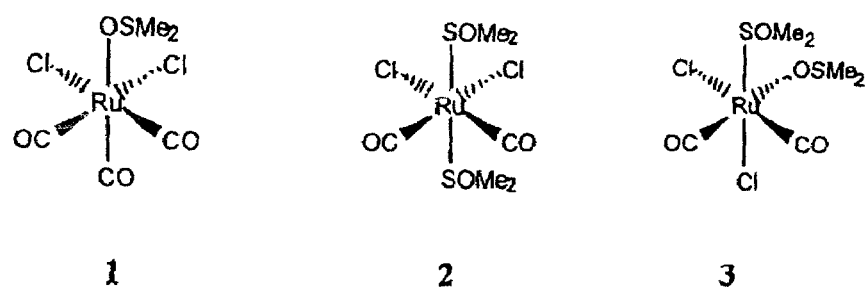

Further studies were conducted on the chemistry of transition metal carbonyls using NMR spectroscopy. The $^{13}C$ NMR spectrum showed that $[Ru(CO)_3Cl_2]_2$ freshly dissolved in DMSO does not exist as a dimer; in fact, two distinct sets of signals corresponding to the known tricarbonyl (1) and di-carbonyl (2) monomers (see formulae in FIG. 3) could be identified. The NMR analysis reveals that, during the solubilization process, DMSO acts as a coordinated ligand to ruthenium thereby promoting the formation of the monomers.

FIG. 3a shows a 100.62 MHz $^{13}C\{^1H\}$ NMR spectrum taken during the first 23 min of the reaction between freshly prepared $[RuCl_2(CO)_3]_2$ and $d_6$-DMSO. The solution very slowly produced fine bubbles of a gas, presumably CO, implied by the formation of compound 2. When the experiment was repeated by dissolving initially the metal complex in DMSO and then diluting with $CDCl_3$, the assignment of the signals coincided with the published $^{13}C(CO)$ chemical shifts of fac-$[RuCl_2(CO)_3(DMSO)]$ (1, δ 183.0, 186.8), cis, cis, trans-$[RuCl_2(CO)_2(DMSO)_2]$ (2, δ 185.0) and cis, cis, cis-$[RuCl_2(CO)_2(DMSO)_2]$ (3, δ 186.0, 191.9) (46). FIG. 3b shows a 100.62 MHz $^{13}C\{^1H\}$ NMR spectrum taken after $[RuCl_2(CO)_3]_2$ in $d_6$-DMSO was warmed at 50° C. for 5 min and left to accumulate overnight. In addition to the peaks that could be assigned to compounds 1, 2 and 3, there are carbonyl signals at δ 187.9 and 190.5 due to unidentified species.

The detection of di-carbonyl monomers demonstrates that CO is liberated; the $^{13}C$ NMR spectrum also suggests that the ratio between compounds 1 and 2 is 40:60.

In sections C and D below, we refer for convenience to $[Ru(CO)_3Cl_2]_2$, but as explained here, when dissolved in DMSO other species are actually present.

C. Effect of $[Ru(CO)_3Cl_2]_2$ on Cell Viability

As there are no precedent studies on the use of metal carbonyl complexes in biological systems, it was necessary to evaluate the potential cytotoxic effect of these compounds. Therefore, the viability of cells in culture was determined after short or prolonged exposure to various concentrations of metal carbonyls.

Rat vascular smooth muscle cells were obtained from the Coriell Cell Repository (Camden, N.J., USA) and grown in Dulbecco's Minimal Essential Medium (MEM) supplemented with 20% foetal calf serum, 2×MEM vitamins, 2×MEM non-essential and essential amino acids, penicillin (100 units/ml) and streptomycin (0.1 mg/ml), Confluent cells were treated with different concentrations of metal carbonyl (introduced as DMSO solution—see section B) for various times and cell viability was assessed using a calorimetric assay kit from Promega (Madison, Wis., USA) as previously described (47) after 3 or 24 h incubation, or after 3 h exposure to the agents followed by 21 h incubation in complete media. Results are expressed as the mean±s.e.m of 6 independent experiments and differences were considered statistically significant at $P<0.05$ (*).

Exposure of $[Fe(CO)_5]$ to light gradually resulted in deposition of a green-brown precipitate, and so viability studies on this metal carbonyl were not pursued. Nevertheless, $[Fe(SPh)_2(2,2'\text{-bipyridine}) (CO)_2]$ proved to elicit a marked vasodilatory effect (see below).

Figure 4A:
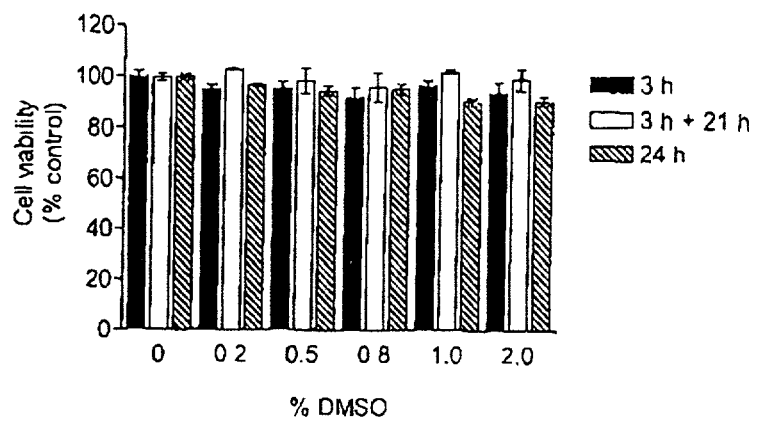
FIG. 4 shows viability data for cells treated with metal carbonyl compounds.
Figure 4B:
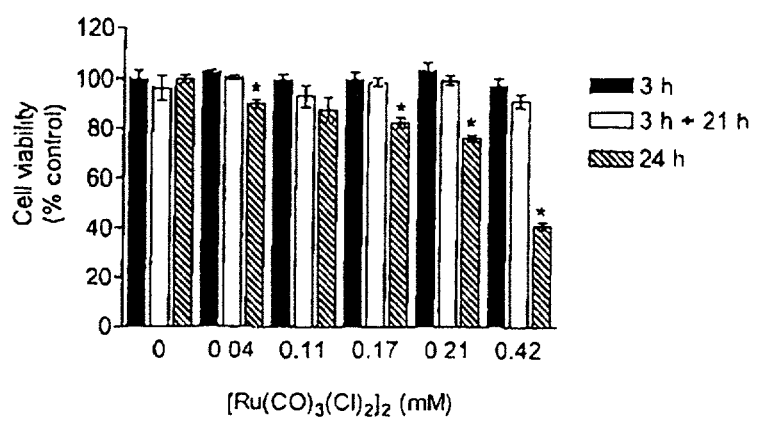

As shown in FIG. 4b, treatment of vascular smooth muscle cells for 3 h with $[Ru(CO)_3Cl_2]_2$ (0–420 µM final concentration) did not promote any detectable cytotoxicity. Similarly, cell viability was well preserved after exposure to this metal carbonyl for 3 h followed by an additional 21 h incubation in complete medium. A pronounced cytotoxic effect (>50% loss in cell viability) was only apparent after prolonged exposure (24 h) to very high concentrations (>400 µM) of $[Ru(CO)_3Cl_2]_2$.

Figure 4C:
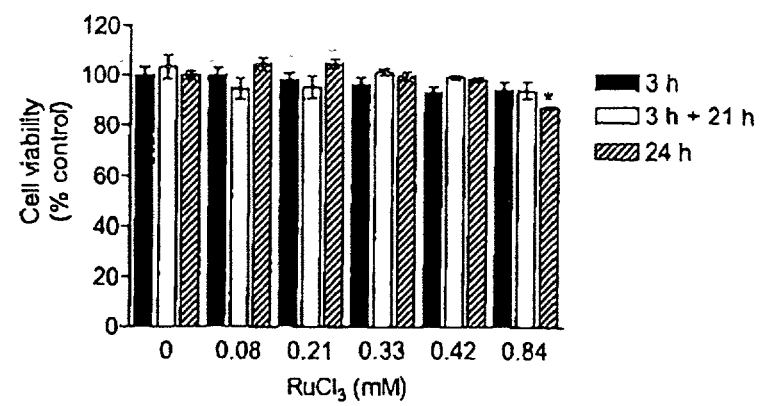

Treatment of cells with the same amounts of vehicle (DMSO) or equivalent molar concentrations of ruthenium $[RuCl_3]$ did not cause any appreciable decrease in cell viability over time (FIGS. 4a and 4c, respectively) indicating that neither the vehicle nor the metal are responsible for the observed cytotoxic effect of $[Ru(CO)_3Cl_2]_2$.

In the case of $[Mn_2(CO)_{10}]$ (0–100 µM), no major cytotoxicity on smooth muscle cells was detected after exposure for 24 h in complete medium (data not shown).

D. Vasodilatory Effect of CO Released from $[Ru(CO)_3Cl_2]_2$

It has previously been demonstrated that increased endogenous CO as a result of HO-1 induction in rat aortas markedly attenuates vasoconstriction (23). To investigate whether CO released from metal carbonyl complexes evokes specific biological activities, we first assessed the effect of these complexes on vessel contractility using the isolated aortic ring model.

Transverse ring sections of thoracic aorta were isolated from male Lewis rats and suspended under a 2 g tension in an organ bath containing oxygenated Krebs-Henseleit buffer at 37° C. as previously described (23). The relaxation response to cumulative doses of metal carbonyl (dissolved in DMSO—see section B) was assessed in aortic rings pre-contracted with phenylephrine (3 µM). Control rings were similarly treated by adding equal doses of DMSO (vehicle) to the organ bath. Results are shown in Table 1 and FIG. 5.

Figure 5:
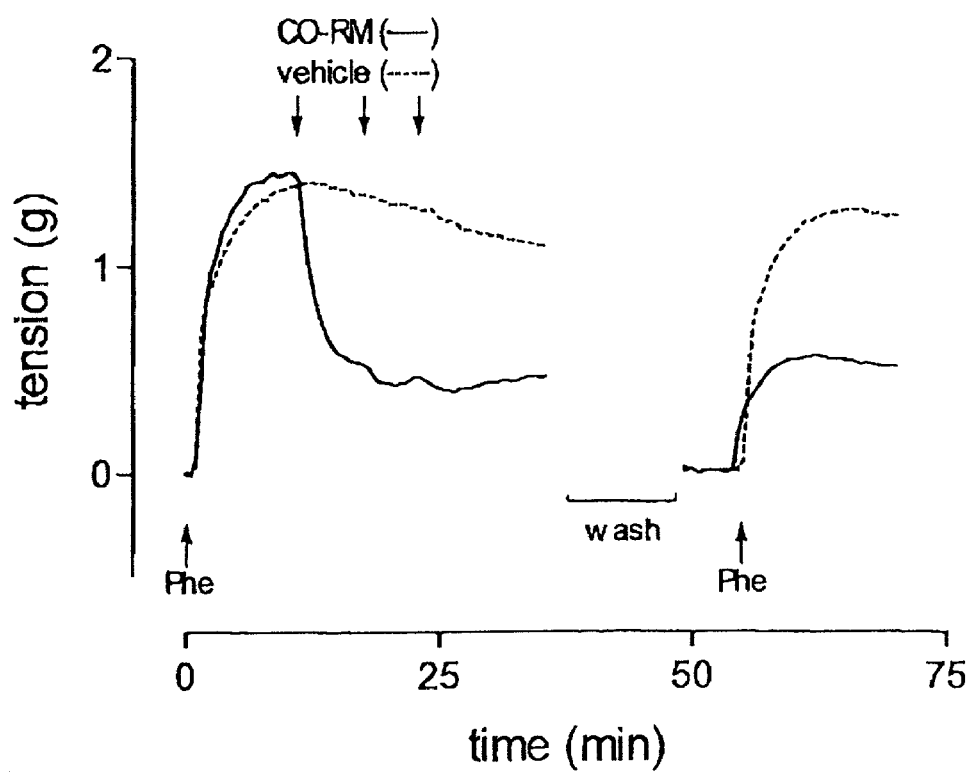
FIG. 5 shows relaxation of aortic rings on treatment with metal carbonyl complexes.

As shown in FIG. 5, consecutive additions of $[Ru(CO)_3Cl_2]_2$ (222 µM final concentration) to aortic rings pre-contracted with phenylephrine elicited a rapid and significant vasodilatation ($P<0.05$); the extent of relaxation was already pronounced after the first addition of the compound (45% more than control). Interestingly, after extensive washing, the phenylephrine-induced contraction was completely restored in control but not in $[Ru(CO)_3Cl_2]_2$-treated vessels indicating that this compound produces long-lasting effects.

The vasodilatory response mediated by metal carbonyls was almost totally abolished when reduced Mb (150 µM), which avidly binds CO, was added to the buffer. Collectively, these findings are consistent with the fact that CO released from metal carbonyls possesses vasoactive properties.

As shown in Table 1, $[Ru(CO)_2(DMSO)_2Cl_2]$ also produced vasodilatation although the effect was less pronounced compared to $[Ru(CO)_3Cl_2]_2$. Interestingly, while $[Ru(CO)_3Cl_2(\text{cytosine})]$ did not demonstrate any effect during the time duration of this experiment, $[Ru(CO)_3(\text{glycinato})Cl]$ elicited significant vasodilatation which is consistent with the high release of CO detected with the MbCO assay. Notably, $[Fe(SPh)_2(2,2'\text{-bipyridine}) (CO)_2]$ which did not release any detectable CO to myoglobin, was still very effective in promoting vasorelaxation. On the other hand, the effect of $[Fe(SPh)_2(H_2NCH_2CH_2NH_2) (CO)_2]$ was less evident.

TABLE 1

| Treatment | % Relaxation | | |
| --- | --- | --- | --- |
| | 1st addition | 2nd addition | 3rd addition |
| Vehicle (DMSO) | 5.7 ± 0.9 | 11.4 ± 1.1 | 18.1 ± 2.5 |
| [Ru(CO)$_3$Cl$_2$]$_2$ | 49.9 ± 2.7* | 66.2 ± 3.2* | 74.1 ± 4.1* |
| [Ru(CO)$_3$Cl$_2$]$_2$ + Mb | 4.0 ± 0.9† | 8.6 ± 0.4† | 15.5 ± 0.4† |
| [RU(CO)$_3$Cl$_2$]$_2$ + ODQ | 7.1 ± 1.1† | 23.6 ± 3.8*† | 55.5 ± 6.9*† |
| [Ru(CO)$_2$(DMSO)$_2$Cl$_2$] | 1.6 | 16 | 35 |
| [Ru(CO)$_3$Cl$_2$(cytosine)] | 3.2 | 10.3 | 12.6 |
| [Ru(CO)$_3$(glycinato)Cl] | 36 | 66.6 | 68.3 |
| [Fe(SPh)$_2$(2,2'-bipyridine)(CO)$_2$] | 50.8 | 60.5 | 75 |
| [Fe(SPh)$_2$(H$_2$NCH$_2$CH$_2$NH$_2$)(CO)$_2$] | 11 | 24.6 | 29.3 |

*$P < 0.01$, compared to vehicle; $P < 0.01$ compared to [RU(CO)$_3$Cl$_2$]$_2$.

Because CO is thought to modulate signal transduction mechanisms via increased production of cGMP, we investigated the effect of a selective inhibitor of guanylate cyclase (ODQ, 10 µM) on vessel contractility. As expected, ODQ considerably reduced the vasodilatation observed after the first two additions of $[Ru(CO)_3Cl_2]_2$; however, it is of interest that the third addition of $[Ru(CO)_3Cl_2]_2$ still elicited a substantial vasodilatory action despite the presence of ODQ Thus, the quanylate cyclase-cGMP pathway appears to be involved in the relaxation caused by this metal carbonyl complex E. Expression of Heme Oxygenase in Rat Tissues As a background to the experiments below, we conducted the following procedure to demonstrate the effect of stimulating CO production endogenously by treating animals with hemin.

For immunohistochemistry analysis, sections of heart muscles (5 μm thickness) were treated with 0.3% $H_2O_2$ in methanol to block endogenous peroxidase activity. Immunohistochemical staining was performed using rabbit polyclonal antibody against HO-1 (1:1000 dilution) as previously described (23). The presence of HO-1 was indicated by the development of a brown color. For Northern blot analysis, cardiac tissue was ground in a mortar under liquid nitrogen and suspended in guanidinium thiocyanate lysis buffer. Total RNA was then extracted using a modification of the method described by Chomczynski and Sacchi (49). RNA was run on a 1.3% denaturing agarose gel containing 2.2 M formaldehyde and transferred onto a nylon membrane overnight. The membrane was hybridized using $[\alpha^{-32}P]dCTP$-labelled cDNA probes to rat HO-1 and GAPDH genes and bands analyzed using a densitometer as previously described (23, 50).

Hearts were removed from Lewis rats 24 h after treatment with vehicle (control) or hemin (75 μmol/kg, i.p.) and immunostaining for HO-1 was assessed. For Northern blot analysis, rats were treated with hemin (75 μmol/kg, i.p.) and hearts removed at different time points to assess HO-1 mRNA levels (+ve, positive control).

Figure 7:
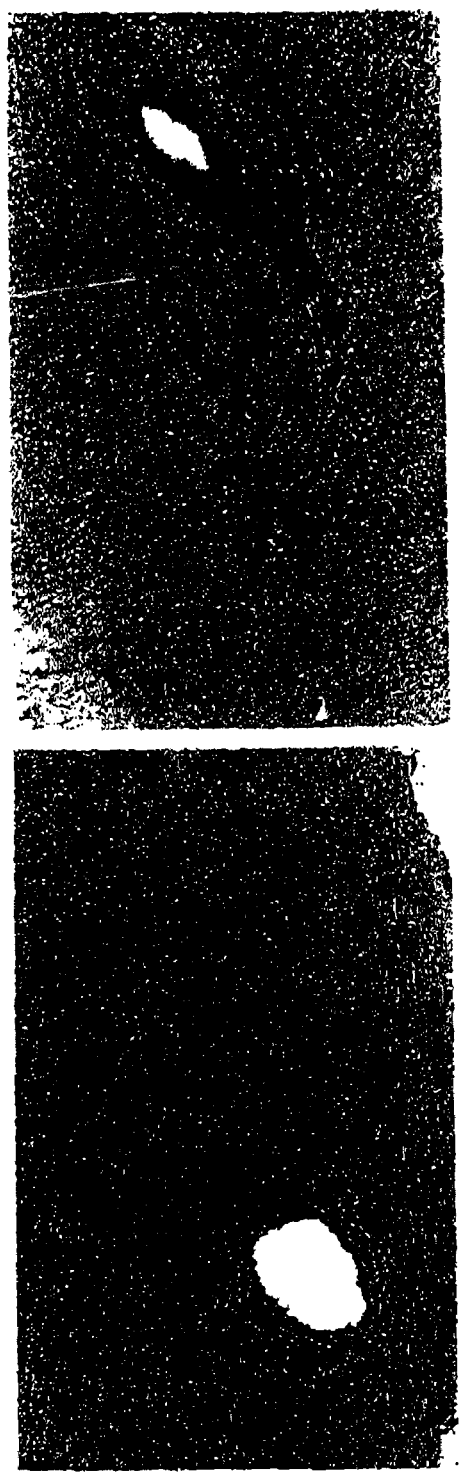
FIG. 7 shows expression of heme oxygenase 1 in rat hearts.
Figure 7:
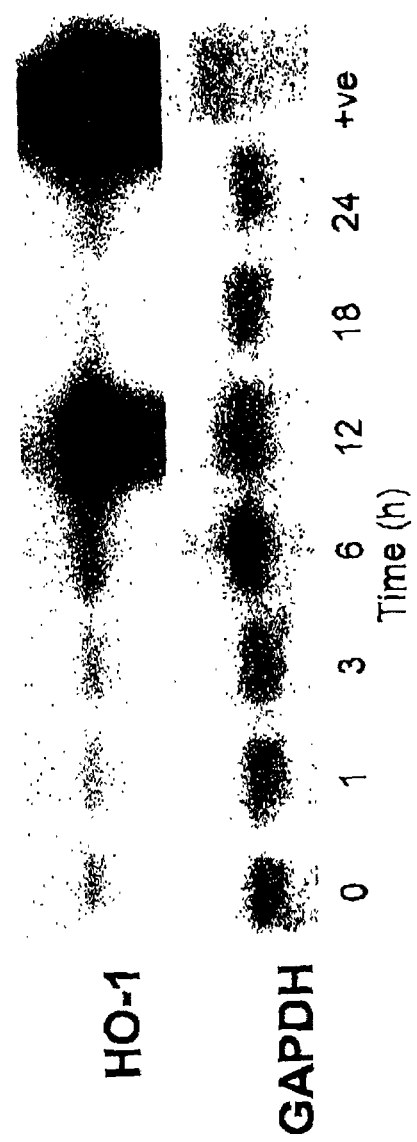

FIG. 7 confirms that HO-1 protein (7a) and mRNA (7b) are highly expressed in hearts 24 h after hemin treatment; interestingly, the immunostaining for HO-1 protein was primarily confined to the vessels of cardiac muscle (FIG. 7a, right panel).

F. Attenuation of Vasoconstriction by Metal Carbonyls in Perfused Heart

Additional experiments were conducted to determine the biological activity of metal carbonyls on vascular function in vivo and compare it with HO-1-derived CO, by monitoring their effects on changes in coronary perfusion pressure (CPP) of isolated rat hearts.

Langendorff heart preparations were performed using male Lewis rats (300–350 g) as previously described by our group (35). Hearts were excised, the aorta cannulated and retrograde perfusion was established at a constant flow of 15 ml/min using Krebs-Henseleit buffer (in mM: 119 NaCl, 4.7 KCl, 2.5 $CaCl_2$, 1.66 $MgSO_4$, 24.9 $NaHCO_3$, 1.18 $KH_2PO_4$, 5.55 glucose, 2.00 sodium pyruvate, 0.5 EGTA) bubbled with 95% $O_2$ and 5% $CO_2$ at 37° C. (pH 7.4). Coronary perfusion pressure (CPP), a parameter indicative of coronary vessel contractility, was continuously measured by a pressure transducer connected to the aortic cannula and data analyzed with an Acknowledge software (BIOPAC System Inc.).

Hearts removed either from control rats (vehicle-treated) or from animals that were pre-treated with the heme oxygenase-1 inducer hemin (75 μmol/kg, i.p.) the day before, were initially equilibrated for 20 min on the Langendorff apparatus and then perfused with L-NAME (25 μM final concentration) to elicit vasoconstriction. The extent of CPP increase by L-NAME was also monitored over time in hemin-treated animals that received a heme oxygenase inhibitor (SnPPIX, 40 μmol/kg) 1 h prior to heart excision and in control hearts that were perfused with buffer supplemented with $[Mn_2(CO)_{10}]$ (13 μM final concentration). Since $[Mn_2(CO)_{10}]$, releases CO only by photodissociation, Krebs buffer containing $[Mn_2(CO)_{10}]$ was exposed to a cold light source immediately before to entering the aortic cannula.

Figure 6:
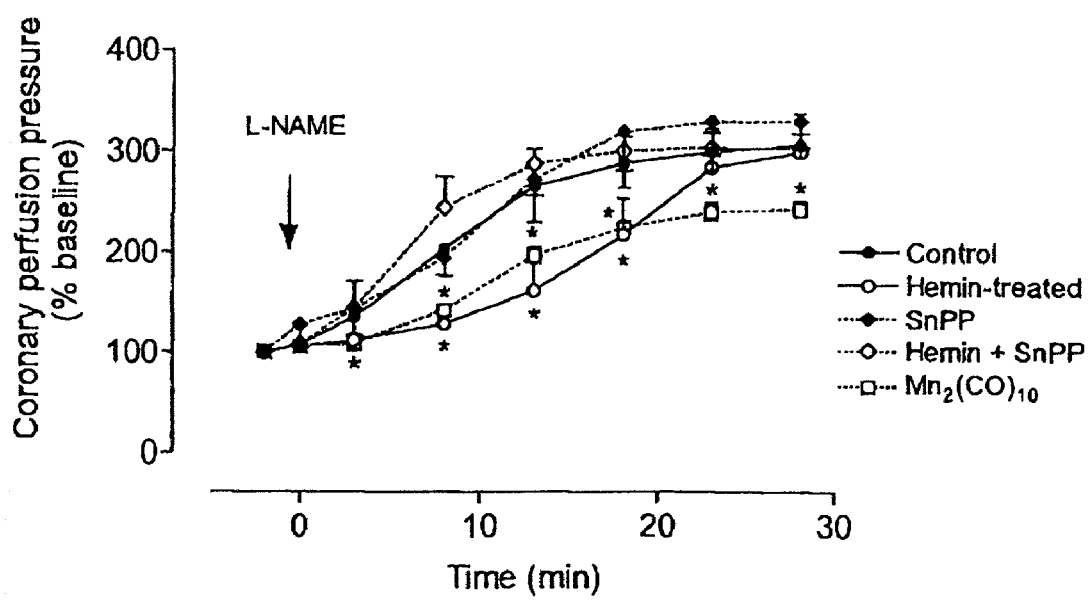
FIG. 6 shows the effects of various treatments on perfused rat hearts.

Vasoconstriction was elicited by perfusion with L-NAME and the extent of CPP increase measured over time. As shown in FIG. 6, L-NAME caused a time-dependent increase in CPP, which reached a maximum (3-fold) after 30 min. Notably, perfusion of hearts with light-stimulated $[Mn_2(CO)_{10}]$ (13 μM) significantly delayed vasoconstriction and maintained CPP at much lower levels at the end of perfusion. When the buffer containing $[Mn_2(CO)_{10}]$ was not exposed to light, thus omitting the CO-induced release process, the extent of constriction mediated by L-NAME was unaffected (data not shown); in addition, perfusion with manganese chloride (negative control) had no effect on myocardial CPP (data not shown).

The effect observed with $[Mn_2(CO)_{10}]$ could be similarly reproduced by induction of HO-1 in heart tissue by pretreatment with hemin. It has previously been reported that treatment of rats with hemin results in increased production of cardiac bilirubin, which is equimolar to endogenously generated CO (35). The rise in CPP mediated by L-NAME in hemin-treated hearts was markedly attenuated (P<0.05), to an extent similar to that produced by $[Mn_2(CO)_{10}]$ (FIG. 6); predictably, the effect of hemin was completely reversed by tin protoporphyrin IX (SnPPIX), a heme oxygenase inhibitor. Thus, the vasoactive properties of the HO-1/CO pathway can be simulated by $[Mn_2(CO)_{10}]$.

Results are means±s.e.m. of 6 independent experiments. *P<0.05 vs. vehicle-treated group (control).

G. Animal Studies

Since it has previously been reported that HO-1-derived CO also prevents acute hypertension in vivo (40), experiments were performed to examine the effectiveness of metal carbonyls in regulating mean arterial pressure in animals.

Lewis rats (280–350 g) were anaesthetised by intramuscular injection of 1 ml/kg Hypnorm (fentanyl 0.315 mg/ml and fluanisone 10 mg/ml) followed 5 min later by an intraperitoneal injection of 5 mg/kg diazepam. Specially designed femoral artery and venous catheters were then surgically implanted as previously described (40). The arterial cannula was connected to a Grass pressure transducer and blood pressure monitored continuously using a polygraph recorder. Experiments were conducted on anaesthetized animals and recordings were made within 30 min of the surgical procedure.

Figure 8:
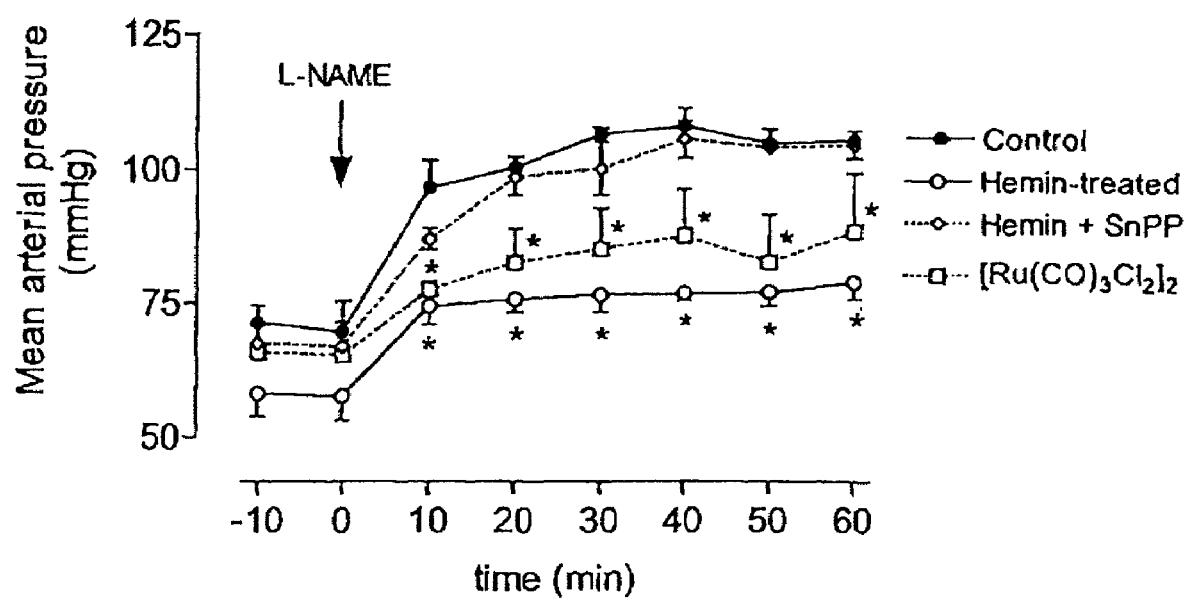
FIG. 8 shows the effects of various treatments on rat mean arterial pressure.

Control rats (vehicle-treated) and animals that were pretreated with hemin (75 μmol/kg, i.p) 24 h prior to blood pressure monitoring were then administered with an intravenous injection of 30 μmol/Kg L-NAME to elicit an increase in mean arterial pressure. The extent of blood pressure increase by L-NAME was also monitored over time in hemin-treated animals that received SnPPIX (40 μmol/kg, i.p.) and in control rats previously injected with $[Ru(CO)_3Cl_2]_2$ (60 μmol/kg, i.v.). In these two groups, SnPPIX or $[Ru(CO)_3Cl_2]_2$ were administered to animals 1 h prior to L-NAME injection. Results are shown in FIG. 8.

Intravenous infusion of L-NAME in rats produced a rapid and significant increase in blood pressure (P<0.05); this effect was markedly suppressed by pre-treatment of animals with a single infusion of $[Ru(CO)_3Cl_2]_2$ prior to L-NAME administration. Moreover, and in analogy with the data on coronary vasoconstriction in isolated hearts, treatment of animals with hemin resulted in a significant suppression of the L-NAME-mediated hypertensive responses, which once again was totally reversed by blockade of the heme oxygenase pathway with SnPPIX. Results are the means±s.e.m. of 5 independent experiments. *P<0.05 vs. vehicle-treated group (control). Collectively, these in vivo findings attest a consistent and reproducible biological activity of metal carbonyls through their ability to carry and deliver CO.

H. Further Studies on CO Release

The myoglobin assay procedure of section A above was carried out on many other metal-carbonyl complexes, to determine the amount of CO release and information on the kinetics of CO release. The compounds and the results are tabulated in FIGS. 9a to 9f. The compounds include [Ru(CO)$_3$Cl$_2$]$_2$ also tested in section A and complexes related to it. The applicants' internal reference numbers are used for convenience.

To obtain the data in FIGS. 9a to 9f the carbonyl compounds (CO-RMs) were solubilized in water or DMSO as indicated and added immediately to a solution of myoglobin (66 μM) in phosphate buffer (pH=7.4). Two different concentrations were tested for each CO-RM (20 and 40 μM) and the conversion of myoglobin to carbon monoxide myoglobin (MbCO) was measured spectrophotometrically at different time points (0, 10, 20 and 30 min). MW=molecular weight. PPT indicates that a precipitate formed. N.D.="not detectable".

The CO release data of section A above and FIGS. 9a to 9f shows that selection of the ligands modulates CO release, both as to amount released and rate of release, permitting selection of release properties, which is important for targeting a specific biological effect.

I. Effect of CO-RM-3 (Ru(CO)$_3$Cl(glycinato)) on Systemic Blood Pressure and Heart Rate in Anaesthatised Rats Adult male Sprague-Dawley rats (280–350 g, 8–10 weeks of age) were bred in-house at the Northwick Park Institute for Medical Research (Harrow, UK). Rats were housed in groups of 3 in cages under a 12 h cycle of day/night, with free access to drinking water and fed ad libitum. All surgical procedures were performed in compliance with U.K. Home Office regulations. Rats were anaesthetised in a polycarbonate chamber in a stream of Enflurane™ (Abbot, UK) in oxygen before being transferred onto a mask and continuously supplied with Enflurane™ throughout the experiment with an anaesthetic machine (Airmed, UK). During the surgical procedure the rats were kept at a constant body temperature of 37° C. using a heat pad positioned underneath the operating surface. Specially designed femoral artery and venous catheters were then surgically implanted as previously described (see ref. 40). The catheter in the artery was connected via a luer connector and a three-way tap to a pressure transducer (Gould model P23$_{ID}$, Statham, USA) for continuous mean arterial pressure (MAP) and heart rate (HR) monitoring. A purpose-built tail-cuff pressure transducer (ADInstruments, UK) was also placed on the tail of the rat and pressure transducer and tail cuff were connected to a polygraph recorder (Grass Model 7D, Astramed, UK) pre-calibrated in millimeters of mercury (mmHg). An analogue output provided data for a computer-based data acquisition system (PowerLab™, ADInstruments, UK). The computer-based system was set to record mean arterial pressure (MAP), in mmHg, and heart rate (HR), in beats/min (bpm), for the duration of the experiment. A period of 20 minutes was allowed after surgery during which time anaesthetic supply was adjusted so that each animal had a stable resting MAP of around 80 mmHg (n=16, mean=81.5 mmHg). Once a stable pressure had been reached, each catheter was flushed with saline containing heparin and no further changes were made to the anaesthetic supply. Ru(CO)$_3$Cl(glycinato) (CO-RM-3) was prepared in stock solutions of 20, 60 and 120 μmoles.ml$^{-1}$ by solubilizing the compound in saline. Cis-RuCl$_2$(DMSO)$_4$, which does not contain any carbonyl groups, was used as a 'negative control'. CO-RM-3 (or the negative control) was then infused into the animal via the femoral vein catheter as a bolus so that the final concentration infused was 10, 30 or 60 μmoles.kg$^{-1}$ body weight. Throughout the experiment MAP and HR were continuously recorded and monitored. Although concentrations of 10, 30 and 60 μmoles.kg$^{-1}$ were infused into each animal, the resulting concentrations in the animal were cumulative. Therefore, the final concentration attained in the animal was 10, 40 and 100 μmoles.kg$^{-1}$, respectively.

The results are presented in Table 2, where the data shown represents samples taken at baseline (just before infusion of the compound) and directly after administration of 10, 30 and 60 μmoles.kg$^{-1}$ of the compound. All data are mean±SEM. n=3 independent experiments. *P<0.05 vs. baseline.

Cis-RuCl$_2$(DMSO)$_4$ (control) had no significant effects on either HR or MAP at any of the concentrations used (10, 30 or 60 μmoles.kg$^{-1}$). Even after the final (60 μmoles.kg$^{-1}$) infusion of Cis-RuCl$_2$(DMSO)$_4$, the MAP (81±4 mmHg) and HR (256±9 bpm) were well preserved compared to baseline measurements (80±2 mmHg and 257±7 bpm, respectively). There was a marginal increase (5.5±1 mmHg) in MAP during the administration of each bolus of the compound. However, this effect is believed to be associated with a volume increase since it also occurred when saline was infused during the inserting procedure. In contrast, administration of Ru(CO)$_3$Cl(glycinato) resulted in a concentration-dependent transient decrease in MAP followed by a return to baseline over a period of 10 min; with 10, 30 and 60 μmoles.kg$^{-1}$ bolus infusions resulting in 6±2, 8±3 and 14±0.3 (P<0.05) mmHg decreases, respectively. As before, HR remained unchanged (253±23 bpm) compared to baseline (270±20 bpm). These data demonstrate that CO liberated from CO-RM-3 can modulate blood pressure and can be used therapeutically to control acute and chronic hypertensive responses in vivo. These data parallel the evidence that endogenous CO generated from activated heme oxygenase-1 is a potent vasodilator and suppresses acute hypertension in vivo (see ref. 23 and 40).

TABLE 2

| Compound | Baseline | | 10 μmol.kg$^{-1}$ | | 30 μmol.kg$^{-1}$ | | 60 μmol.kg$^{-1}$ | |
| --- | --- | --- | --- | --- | --- | --- | --- | --- |
| | HR (bpm) | MAP (mmHg) | HR (bpm) | MAP (mmHg) | HR (bpm) | MAP (mmHg) | HR (bpm) | MAP (mmHg) |
| Cis-RuCl$_2$(DMSO)$_4$ (negative control) | 257 ± 7 | 80 ± 2 | 255 ± 6 | 82 ± 4 | 256 ± 8 | 79 ± 5 | 256 ± 9 | 81 ± 4 |
| Ru(CO)$_3$Cl(glycinato) (CO-RM-3) | 270 ± 20 | 79 ± 2 | 276 ± 20 | 73 ± 2 | 261 ± 22 | 72 ± 7 | 253 ± 23 | 65 ± 4* |

J. Effect of Ru(CO)$_3$Cl(Glycinato) on Cardiac Transplant Rejection in Mice

Hearts from male BALB/c mouse (25–30 g) were used as donor organs for transplantation into male CBA mice (25–30 g). Mice were housed in groups of 3 in cages under a 12 h cycle of day/night, with free access to drinking water and fed ad libitum. All surgical procedures were performed in compliance with U.K. Home Office regulations. Animals were anaesthetized by an intraperitoneal injection of ketamine/xylazine during all procedures. The surgical technique involved the transplantation of the cardiac allograft into the recipient's neck as previously described (51). Graft survival was assessed daily by palpation, and rejection was diagnosed by cessation of ventricular contractions.

Ru(CO)$_3$Cl(glycinato) was dissolved in 0.1 ml saline and administered intraperitoneally. All doses are 40 mg/kg of Ru(CO)$_3$Cl(glycinato). The donors received two doses of Ru(CO)$_3$Cl(glycinato) respectively at 1 day and 15 min prior to cardiac harvest. The recipients received doses of Ru(CO)$_3$Cl(glycinato) at 1 day before surgery, 30 min prior to cardiac reperfusion and 1 h after transplantation (Day 0). Thereafter, graft recipients received a daily dose of Ru(CO)$_3$ Cl(glycinato) from day 1 to day 8 (inclusive) post-transplant. In the control group, recipients received an equivalent dose of saline (vehicle) 1 day before and each day (days 1 to 8) after cardiac transplantation. Carprofen (0.01 mg) was given subcutaneously for pain relief immediately after transplantation to all animals. The results of this study are shown in FIG. 10. n=5 for each group. *p<0.002 vs. control. BALB/c hearts trasplanted into CBA mice following treatment with saline (control group) underwent rejection very rapidly. 100% of hearts stopped beating within 9 days of transplantation. In contrast, the survival time of hearts transplanted into mice receiving Ru(CO)$_3$Cl(glycinato) was significantly prolonged (p<0.002) with 100% of hearts still beating 18 days after transplantation. At 25 days after heart transplantation, 60% of mice treated with Ru(CO)$_3$Cl(glycinato) still did not show any sign of rejection (p<0.002) and at 30 days 40% of transplanted hearts were still viable. These data demonstrate that Ru(CO)$_3$Cl(glycinato) is very effective in prolonging the survival of murine cardiac grafts and attenuating organ rejection. The result is in parallel with recently published reports showing that mice treated with CO gas (by inhalation) are significantly less susceptible to graft rejection in a model of mouse-to-rat cardiac transplant (51).

Based on the findings above on CO release and vasorelaxation, the data in this section indicates that CO liberated from the carbonyl complex mediates the anti-rejection process.

K. Effect of Ru(CO)$_3$Cl(Glycinato) on Nitric Oxide Production in Macrophages Following Endotoxin Challenge The signaling molecule nitrogen monoxide (NO), which is generated in mammals by a family of constitutive (nNOS and eNOS) and inducible (iNOS) NO synthase enzymes, plays an essential regulatory role in a variety of physiological and pathophysiological processes that take place within the cardiovascular, nervous and immune systems (52). Overproduction of NO has been established as a potent cytotoxic weapon in host defense against infection, inflammation and cancer. Considerable amounts of NO can originate from activated iNOS when appropriately induced by cytokines, endotoxins or lipopolysaccharide (LPS), oxygen free radicals or other stressful stimuli (53). In particular, macrophages are a specific target of pro-inflammatory stimuli as they highly express iNOS and can generate excessive amounts of NO to modulate important cytostatic/bactericidal actions.

From unpublished data, it has been postulated that induction of the heme oxygenase-1 (HO-1)/bilirubin/CO pathway represents a counter-regulatory system against the deleterious effects elicited by overproduction of NO. Specifically, both CO and bilirubin may interfere with NO generation by acting as inhibitors of NOS activity and scavenger of NO, respectively. CO gas has been shown to inhibit NOS activity in various tissues (54), and it has been suggested that bilirubin can directly interact with NO and NO-related species (55).

The present study was undertaken to assess the effect of Ru(CO)$_3$Cl(glycinato) (CO-RM-3) on the production of NO from endotoxin-stimulated macrophages. Mouse RAW 264.7 macrophages were cultured in 24 wells using DMEM medium. Confluent cells were incubated for 24 h with E. coli lipopolysaccharide (LPS, 3 μg/ml) in the presence or absence of increasing concentrations of CO-RM-3 (10, 50 and 100 μM). Control cells were exposed to culture medium alone. Nitrite in the culture medium was measured as an index of NO production using the Griess reagent method (56). Cell viability was also assessed in macrophages 24 h after treatment with the various agents as described in reference 47. Treatment of macrophages with LPS caused a significant increase in nitrite levels (p<0.05) after 24 h incubation (see FIG. 11, where bars represent the mean±S.E.M. of 6 independent experiments. *p<0.05 vs. control; +p<0.05 vs. LPS. The presence of CO-RM-3 significantly attenuated nitrite generation in a concentration dependent manner. As shown in FIG. 12 (where bars represent the mean±S.E.M. of 6 independent experiments), these treatments did not affect cell viability as no toxic effect was observed at the end of the incubation period.

These data indicate in the ability of CO released from CO-RM-3 to prevent the inflammatory response in macrophages by inhibiting the production of iNOS-derived NO. Furthermore, and in line with the beneficial effects shown by CO-RM-3 on blood pressure and cardiac graft rejection, these results suggest a potential therapeutic application of water-soluble CO carriers in the modulation of vascular- and inflammatory-related pathological states.

L. Syntheses

Synthetic methods for obtaining compounds of FIGS. 9a to 9f tested for CO release will now be described. Purity of the product has not been investigated in detail. Stereoisomers are expected to be present.

Preparation of Ru(CO)$_3$Cl(NH$_2$CH$_2${CH$_2$SH}CO$_2$)[M$_R$ 340.5]

L-Cysteine Complex. Reference Number: CO-RM-26

[Ru(CO)$_3$Cl$_2$]$_2$ (0.129 g, 0.25 mmol) and L-cysteine (0.039 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to given an orange solid (0.120 g, 70%).

Preparation of Ru(CO)$_3$Cl(NH$_2$CH$_2$CO2)[M$_R$ 294.5]

Glycine Complex. Reference Number: CO-RM-3

[Ru(CO)$_3$Cl$_2$]$_2$ (0.129 g, 0.25 mmol) and glycine (0.039 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a pale yellow solid (0.142 g, 96%).

Preparation of Ru(CO)$_3$Cl(NH$_2$CH{CHMeCH$_2$CH$_3$}CO$_2$) [$M_R$ 350.5]

DL-Isoleucine Complex. Reference Number: CO-RM-38.

[Ru(CO)$_3$Cl$_2$]$_2$ (0.129 g, 0.25 mmol) and DL-isoleucine (0.066 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a yellow solid (0.086 g, 49%).

Preparation of Ru(CO)$_3$Cl(NH$_2$CH{CH$_2$OH}CO$_2$)[$M_R$ 324.5]

L-Serine Complex. Reference Number: CO-RM-39.

[Ru(CO)$_3$Cl$_2$]$_2$ (0.129 g, 0.25 mmol) and L-serine (0.053 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a pale yellow solid (0.095 g, 59%)

Preparation of Ru(CO)$_3$Cl(NH$_2$CH{CH$_3$}CO$_2$[$M_R$ 308.5]

L-Alanine Complex. Reference Number: CO-RM-40.

[Ru(CO)$_3$Cl$_2$]$_2$ (0.129 g, 0.25 mmol) and L-alanine (0.045 g, 0,50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF, and filtered. The solution was evaporated down to give an orange solid (0.145 g, 94%).

Preparation of Ru(CO)$_3$Cl(NH$_2$CH{CH$_2$CH$_2$CONH$_2$}C0$_2$) [$M_R$ 365.5]

L-Glutamine Complex. Reference Number: CO-RM-42.

[Ru(CO)$_3$Cl$_2$]$_2$ (0.129 g, 0.25 mmol) and L-glutamine (0.073 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF and filtered. The solution was evaporated down to give a yellow oil which solidified under high vacuum to give a pale yellow solid (0.170 g, 93%).

Preparation of RU(CO)$_3$Cl(NH$_2$CH{CH$_2$CH$_2$NHC(=NH)NH$_2$}CO$_2$) [$M_R$ 393.5]

L-Arginine Complex. Reference Number: CO-RM-43.

[Ru(CO)$_3$Cl$_2$]$_2$ (0.129 g, 0.25 mmol) and L-arginine (0.087 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF/MeOH (4:1) and filtered The solution was evaporated down to given an orange solid (0.185 g, 94%).

Preparation of Ru(CO)$_3$Cl (NH$_2$CH{CH$_2$CH$_2$CH$_2$CH$_2$NH$_2$}CO$_2$) [$M_R$ 365.5]

L-Lysine Complex. Reference Number: CO-RM-46.

[RU(CO)$_3$Cl$_2$]$_2$ (0.129 g, 0.25 mmol) and L-lysine (0.073 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF/MeOH (3:1) and filtered. The solution was evaporated down to give a yellow oil which solidified under high vacuum to given an orange solid (0.163 g, 89%).

Preparation of Ru(CO)$_3$Cl(NH$_2$CH{CH(CH$_3$)$_2$}CO$_2$[$M_R$ 336.5]

L-Valine Complex. Reference Number: CO-RM-67.

[Ru(CO)$_3$Cl$_2$]$_2$ (0.129 g, 0.25 mmol) and L-valine (0.059 g, 0.50 mmol) were placed under nitrogen in a round bottomed flask. Methanol (75 cm$^3$) and sodium ethoxide (0.0349, 0.50 mmol) were added and the reaction allowed to stir for 18 hours. The solvent was then removed under pressure and the yellow residue redissolved in THF and filtered. Excess 40-60 light petroleum was added and the solution evaporated down to given a white solid (0.114 g, 68%).

Preparation of Ru(CO)$_3$Cl(NH$_2$CH(CH(OH)CH$_3$)CO$_2$)[$M_R$ 338.5]

L-Threonine Complex. Reference Number: CO-RM-74.

[Ru(CO)$_3$Cl$_2$]$_2$ (0.129 g, 0.25 mmol) and L-threonine (0.0609, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF and filtered. Excess 40-60 light petroleum was added and the solution evaporated down to give a white solid (0.149 g, 88%).

Preparation of [Fe($\eta$-C$_5$H$_5$)(CO)$_3$]Cl [$M_R$ 240.5]

Reference Number: CO-RM-70.

A sodium amalgam was prepared by, under nitrogen in a Schlenk tube, dissolving sodium metal (2.04 g) in mercury (18 cm$^3$). This was allowed to cool to room temperature and tetrahydrofuran (40 cm$^3$) added. Then [FeCp(CO)$_2$]$_2$ (7.08 g, 20.3 mmol) in tetrahydrofuran (60 cm$^3$) added and the flask shaken vigorously for 45 minutes.

Then into a large 3-necked flask purged with nitrogen, THF (300 cm$^3$) and ethyl chloroformate (40 mmol, 4.34 g, 3.84 cm$^3$) were placed and cooled to 0° C. The red-yellow solution of cleaved dimer was then transferred into the round bottomed flask and allowed to stir for one hour at low temperature before being concentrated in volume. The red-brown residue was extracted with benzene (5×20 cm$^3$), the extracts filtered, and HCl gas blown through the solution for 15 minutes. An immediate precipitation was observed, the solution was reduced in volume and the orange precipitate collected, washed with diethyl ether (20 cm$^3$) and dried. (4.84 g, 50%).

Preparation of [Fe($\eta$-C$_5$R$_5$)(CO)$_3$]PF$_6$[$M_R$ 350]

Reference Number: CO-RM-71.

[Fe($\eta$-C$_5$H$_5$)(CO)$_3$]Cl(3.00 g, 12.5 mmol) was dissolved in water (50 cm$^3$) and sodium hexafluorophosphate (2.00 g, leq) in water (50 cm$^3$) added. An orange precipitate was immediately formed, the reaction stirred for 15 minutes and the orange precipitate collected under suction (3.04 g, 70%).

Preparation of Ru(CO)$_3$Cl$_2$(Guanosine) [M$_R$ 540]

Reference Number: CO-RM-17.

[Ru(CO)$_3$Cl$_2$]$_2$ (0.129 g, 0.25 mmol) and guanosine (0.142 g, 0.50 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight. The solvent was pipetted off to leave a white solid which was dried under high vacuum (0.130 g, 48%).

Preparation of [Ru(CO)$_3$Cl(Guanosine)$_2$]/Cl[M$_R$ 824]

Reference Number: CO-RM-18.

[RU(CO)$_3$Cl$_2$]$_2$ (0.129 g, 0.25 mmol) and guanosine (0.284 g, 1.00 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight. The solvent was pipetted off to leave a white solid which was dried under high vacuum (0.220 g, 53%).

Preparation of Ru(CO)$_3$Cl$_2$(Triacetyl-Guanosine) [M$_R$ 666]

Reference Number: CO-RM-29.

[Ru(CO)$_3$Cl$_2$]$_2$ (0.129 g, 0.25 mmol) and 2,3,5-triacetylguanosine (0.205 g, 0.50 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight, The solvent was pipetted off to leave a white solid which was dried under high vacuum (0.212 g, 63%).

Preparation of Ru(CO)$_3$Cl$_2$(Guanine) [M$_R$ 408]

Reference Number: CO-RM-22.

[Ru(CO)$_3$Cl$_2$]$_2$ (0.129 g, 0.25 mmol) and guanine (0.076 g, 0,50 mmol) were placed under nitrogen in a round bottomed flask. Tetrahydrofuran (75 cm$^3$) was added and the reaction allowed to stir for 18 hours. The solution was then reduced in volume to approximately 10 cm$^3$. Excess 40-60 light petroleum was added and the precipitate formed allowed to settle out in the freezer overnight. The solvent was pipetted off to leave a pale yellow solid which was dried under high vacuum (0.082 g, 39%).

Preparation of [Ru(CO)$_3$Cl(Guanine)$_2$]Cl[M$_R$ 558]

Reference Number: CO-RM-23.

[Ru(CO)$_3$Cl$_2$]$_2$ (0.129 g, 0.25 mmol) and guanine (0.152 g, 1.00 mmol) were placed under nitrogen in a round bottomed flask. Tetrahydrofuran (75 cm$^3$) was added and the reaction allowed to stir for 18 hours. The solution was then reduced in volume to approximately 10 cm$^3$. Excess 40-60 light petroleum was added and the precipitate formed allowed to settle out in the freezer overnight. The solvent was pipetted off to leave a cream solid which was dried under high vacuum (0.170 g, 61%).

Preparation of fac-RuCl$_2$(CO)$_3$(THF) [M$_R$ 328]

Reference Number: CO-RM-11.

[Ru(CO)$_3$Cl$_2$]$_2$ (0.380 g, 0.74 mmol) and tetrahydrofuran (5 cm$^3$) were placed in a conical flask and the yellow solution stirred for 15 minutes. Then the solvent was removed under reduced pressure leaving a yellow oil which upon standing solidified. Addition of diethylether (20 cm$^3$) accompanied by sonication afforded a white precipitate and yellow solution. The solid was collected and dried under vacuum (0.134 g, 28%).

Preparation of [RuCl$_2$(CO)$_2$]$_n$[M$_R$ Unknown]

Reference Number: CO-RM-10.

RuCl$_3$×H$_2$O (5.00 g), concentrated hydrochloric acid (25 cm$^3$) and formic acid (25 cm$^3$) were placed in a 3-necked round bottomed flask and the mixture refluxed for 18 hours. The clear yellow solution was then reduced in volume to leave a yellow/orange precipitate, which was transferred into a Soxhlet thimble and extracted overnight with methanol. This solution was then reduced in volume to give an orange oil which solidified under high vacuum to afford an orange precipitate (5.30 g).

Preparation of Ru(CO)$_3$ (O{CH$_2$CO$_2$}$_2$) [M$_R$ 317]

Diglycolic Acid Complex. Reference Number: CO-RM-99.

[Ru(CO)$_3$Cl$_2$]$_2$ (0.129 g, 0.25 mmol) and diglycolic acid (0.067 g), 0.50 mmol) were placed under nitrogen in a round bottomed flask. Methanol (75 cm$^3$) and sodium ethoxide (0.068 g, 1.00 mmol) were aded and the reaction allowed to stir for 18 hours. The solvent was then removed under pressure and the yellow residue redissolved in THF, filtered and excess 40-60 light petroleum added. The yellow solution was evaporated down to give a white solid (0.142 g, 85%).

Preparation of Ru(CO)$_3$ (NH{CH$_2$CO$_2$}$_2$) [M$_R$ 317]

Iminodiacetic Acid Complex. Reference Number: CO-RM-97

[Ru(CO)$_3$Cl$_2$]$_2$ (0.129 g, 0.25 mmol) and iminodiacetic acid (0.066 g, 0.50 mmol) were placed under nitrogen in a round bottomed flask. Methanol (75 cm$^3$) and sodium ethoxide (0.068 g, 1.00 mmol) were added and the reaction allowed to stir for 18 hours. The solvent was then removed under pressure and the yellow residue redissolved in THF/MeOH (4:1), filtered and excess 40-60 light petroleum added. The yellow solution was evaporated down to give an off-white solid (0.140 g, 89%).

Syntheses suitable for CO-RM-1a, CO-RM-1b and the negative controls for these compounds are in reference 57. Synthesis of CO-RM-16 is found in reference 58.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

1. Piantadosi C A. Toxicity of carbon monoxide: hemoglobins vs. histotoxic mechanisms. In: Carbon monoxide. (Edited by Penney D G) 1996; Chapter 8.
2. Sjostrand T. Endogenous formation of carbon monoxide in man under normal and pathological conditions. Scan J Clin Lab Invest 1949; 1:201–14.
3. Coburn R F, Blakemore W S, Forster R E. Endogenous carbon monoxide production in man. J Clin Invest 1963; 42:1172–8.

4. Coburn R F, Williams W J, Forster R E. Effect of erythrocyte destruction on carbon monxide production in man. J Clin Invest 1964; 43:1098–103.
5. Coburn R F, Williams W J, Kahn S B. Endogenous carbon monoxide production in patients with hemolytic anemia. J Clin Invest 1966; 45:460–8.
6. Sjostrand T. The formation of carbon monoxide by in vitro decomposition of haemoglobin in bile pigments. Acta Physiol Scand 1952; 26:328–33.
7. Coburn R F, Williams W J, White P, Kahn S B. The production of carbon monoxide from hemoglobin in vivo. J Clin Invest 1967; 46:346–56.
8. Tenhunen R, Marver H S, Schmid R. Microsomal heme oxygenase. Characterization of the enzyme. J Biol Chem 1969; 244:6388–94.
9. Scharf S M, Permutt S, Bromberger-Barnea B. Effects of hypoxic and CO hypoxia on isolated hearts. J Appl Physiol 1975; 39:752–8.
10. Shibahara S, Muller R, Taguchi H, Yoshida T. Cloning and expression of cDNA for rat heme oxygenase. Proc Natl Acad Sci USA 1985; 82:7865–9.
11. Maines M D, Trakshel G M, Kutty R K. Characterization of two constitutive forms of rat liver microsomal heme oxygenase; only one molecular species of the enzyme is inducible. J Biol Chem 1986; 261:411–9.
12. Cruse I, Maines M D. Evidence suggesting that the two forms of heme oxygenase are products of different genes. J Biol Chem 1988; 263:3348–53.
13. Trakshel G M, Maines M D. Multiplicity of heme oxygenase isozymes: HO-1 and HO-2 are different molecular species in rat and rabbit. J Biol Chem 1989; 264:1323–8.
14. Maines M D. Heme oxygenase; function, multiplicity, regulatory mechanisms, and clinical applications. FASEB J 1988; 2:2557–68.
15. Marks G S, Brien J F, Nakatsu K, McLaughlin B E. Does carbon monoxide have a physiological function? Trends Pharmacol Sci 1991; 12:185–8.
16. Stocker R, Yamamoto Y, McDonagh A P, Glazer A N, Ames B N, Bilirubin is an antioxidant of possible physiological importance. Science 1987; 235:1043–6.
17. McDonagh A F. Is bilirubin good for you. Clin Perinat 1990; 17:359–69.
18. Coceani F, Hamilton N C, Labuc J, Olley P M. Cytochrome P 450-linked monooxygenase: involvement in the lamb ductus arteriosus. Am J Physiol 1984; 246(4 Pt 2):H640–3.
19. Vedernikov Y P, Graser T, vanin A F. Similar endothelium-independent arterial relaxation by carbon monoxide and nitric oxide. Biomed Biochim Acta 1989; 8:601–3.
20, Furchgott R F, Jothianandan D. Endothelium-dependent and -independent vasodilation involving cGMP: relaxation induced by nitric oxide, carbon monoxide and light. Blood Vessels 1991; 28:52–61.
21. Morita T, Perrella M A, Lee M E, Kourembanas S. Smooth muscle cell-derived carbon monoxide is a regulator of vascular cGMP. Proc Natl Acad Sci USA 1995; 92:1475–9.
22. Christodoulides N, Durante W, Kroll M H, Schafer A I. Vascular smooth muscle cell heme oxygenases generate guanylyl cyclase-stimulatory carbon monoxide. Circulation 1995; 91:2306–9.
23. Sammut I A, Foresti R, Clark J E, Exon D J, Vesely M J J, Sarathchandra P, Green C J, Motterlini R. Carbon monoxide is a major contributor to the regulation of vascular tone in aortas expressing high levels of haeme oxygenase-1. Br J Pharmacol 1998; 125:1437–44.
24. Coceani F. Carbon monoxide in vasoregulation: the promise and the challenge. Circ Res 2000; 86(12):1184–6.
25. Feelisch M. The biochemical pathways of nitric-oxide formation from nitrovasodilators: appropriate choice of exogenous NO donors and aspects of preparation and handling of aqueous NO solutions. J Cardiovasc Pharmacol 1991; 17:S 25–33.
26. Feelisch M. The use of nitric oxide donors in pharmacological studies. Naunyn-Schmiedeberg's Arch Pharmacol 1998; 358:113–22.
27. Luscher T F. Endogenous and exogenous nitrates and their role in myocardial ischaemia. Br J Clin Pharmacol 1992; 34 Suppl 1:29S-35S.
28. Saavedra J E, Billiar T R, Williams D L, Kim Y M, Watkins S C, Keefer L K. Targeting nitric oxide (NO) delivery in vivo. Design of a liver-selective NO donor prodrug that blocks tumor necrosis factor-alpha-induced apoptosis and toxicity in the liver. J Med Chem 1997; 40(13):1947–54.
29. Saavedra J E, Southan G J, Davies K M, Lundell A, Markou C, Hanson S R, Adrie C, Hurford W E, Zapol W M, Keefer L K. Localizing antithrombotic and vasodilatory activity with a novel, ultrafast nitric oxide donor. J Med Chem 1996; 39(22):4361–5.
30. Abraham N G, Drummond G S, Lutton J D, Kappas A. The biological significance and physiological role of heme oxygenase. Cell Physiol Biochem 1996; 6:129–68.
31. Foresti R, Motterlini R. The heme oxygenase pathway and its interaction with nitric oxide in the control of cellular homeostasis. Free Rad Res 1999; 31:459–75.
32. Maines M D. The heme oxygenase system: a regulator of second messenger gases. Annu Rev Pharmacol Toxicol 1997; 37:517–54.
33. Soares M P, Lin Y, Anrather J, Csizmadia E, Takigami K, Sato K, Grey S T, Colvin R P, Choi A M, Poss K D, et al. Expression of heme oxygenase-1 can determine cardiac xenograft survival. Nature Med 1998; 4:1073–7.
34. Hancock W W, Buelow R, Sayegh M H, Turka L A. Antibody-induced transplant arteriosclerosis is prevented by graft expression of anti-oxidant and anti-apoptotic genes. Nature Med 1998; 4:1392–6.
35. Clark J E, Foresti R, Sarathchandra P, Kaur H, Green C J, Motterlini R. Heme oxygenase-1-derived bilirubin ameliorates post-ischemic myocardial dysfunction. Am J Physiol Heart Circ Physiol 2000; 278:H643–51.
36. Willis D, Moore A R, Frederick R, Willoughby D A. Heme oxygenase: a novel target for the modulation of inflammatory response. Nature Med 1996; 2:87–90.
37. Bauer M, Pannen B H J, Bauer I, Herzog C, Wanner G A, Hanselmann R, Zhang J X, Clemens M G, Larsen R. Evidence for a functional-link between stress-response and vascular control in hepatic portal circulation. Am J Physiol 1996; 271:G929–35.
38. Fukuda K, Panter S S, Sharp F R, Noble L J. Induction of heme oxygenase-1 (HO-1) after traumatic brain injury in the rat. Neurosci Lett 1995; 199:127–30.
39. Yet S F, Pellacani A, Patterson C, Tan L, Folta S C, Foster L, Lee W S, Hsieh C M, Perrella M A. Induction of heme oxygenase-1 expression in vascular smooth muscle cells. A link to endotoxic shock. J Biol Chem 1997; 272:4295–301.
40. Motterlini R, Gonzales A, Foresti R, Clark J E, Green C J, Winslow R M. Heme oxygenase-1-derived carbon monoxide contributes to the suppression of acute hypertensive responses in vivo. Circ Res 1998; 83:568–77.

41. Otterbein L E, Mantell L L, Chol A M K. Carbon monoxide -provides protection against hyperoxic lung injury. Am J Physiol 1999; 276:L688–94.
42. Otterbein L E, Kolls J K, Mantell L L, Cook J L, Alam J, Choi A M K. Exogenous administration of heme oxygenase-1 by gene transfer provides protection against hyperoxia-induced lung injury. J Clin Invest 1999; 103: 1047–54.
43. Otterbein L E, Bach F H, Alam J, Soares M, Tao Lu H, Wysk M, Davis R J, Flavell R A, Choi A M. Carbon monoxide has anti-inflammatory effects involving the mitogen-activated protein kinase pathway. Nat Med 2000; 6(4):422–8.
44. Engelking P C, Lineberger W C. Laser photoelectron spectrometry of the negative ions of iron and iron carbonyls. Electron affinity determination for the series $Fe(CO)_n$, n=0,1,2,3,4. J Am Chem Soc 1979; 101:5569–73.
45. Herrick R S, Brown T L. Flash photolytic investigation of photoinduced carbon monoxide dissociation from dinuclear manganese carbonyl compounds. Inorg Chem 1984; 23:4550–3.
46. Alessio E, Milani B, Bolle M, Mestroni G, Falechini P, Todone F, Geremia S, Calligaris M. Carbonyl derivatives of chloride-dimethyl sulfoxide-ruthenium(II) complexes: synthesis, structural characterization, and reactivity of $Ru(CO)(DMSO)_{4-x}Cl_2$ complexes (x=1–3). Inorg Chem 1995; 34:4722–34.
47. Clark J E, Foresti R, Green C J, Motterlini R. Dynamics of haem oxygenase-1 expression and bilirubin production in cellular protection against oxidative stress. Biochem J 2000; 348:615–9.
48. Vanin A F. Dinitrosyl iron complexes and S-nitrosothiols are two possible forms for stabilization and transport of nitric oxide in biological systems. Biochemistry (Moscow) 1998; 63(7):782–93.
49. Chomczynski P, Sacchi N. Single step method of RNA isolation by acid guanidinium thiocyanate-phenol-chloroform extraction. Anal Biochem 1987; 162:156–9.
50. Motterlini R, Foresti R, Bassi R, Calabrese V, Clark J E, Green C J. Endothelial heme oxygenase-1 induction by hypoxia: modulation by inducible nitric oxide synthase (iNOS) and S-nitrosothiols. J Biol Chem 2000; 275: 13613–20.
51. Sato K., Balla J., Otterbein L., Smith R. N., Brouard S., Lin Y., Csizmadia E., Sevigny J., Robson S. C., Vercellotti G., Choi A. M., Bach F. H., Soares M. P. Carbon monoxide generated by heme oxygenase-1 suppresses the rejection of mouse-to-rat cardiac transplants. *J. Immunol.* 166:4185–4194, 2001.
52. Moncada S, Palmer R M J, and Higgs E A. Nitric oxide: physiology, pathophysiology, and pharmacology. *Pharmacol Rev* 43: 109–142, 1991.
53. Nathan C. Inducible nitric oxide synthase: what difference does it make? *J Clin Invest* 100: 2417–2423, 1997.
54. White KA et al. Biochemistry 31: 6627–6631, 1992.
55. Kaur H, Green C J and Motterlini R. Interaction of bilirubin and biliverdin with reactive nitrogen species. *Free Rad. Biol. Med.* 27:S78, 1999.
56. Foresti R, Clark J, Green C J, and Motterlini R. Thiol compounds interact with nitric oxide in regulating heme oxygenase-1 induction in the endothelium. Involvement of superoxide and peroxynitrite anions. *J. Biol. Chem.* 272:18411–18417, 1997.
57. G. Pneumatikakis, A. Yannopoulos and J. Markopoulos, *Inorg. Chim. Acta,* 1988, 151, 243.
58. E. Alessio, B. Milani, M. Bolle, G. Mestroni, P. Faleschini, F. Todone, S. Geremia and M. Calligaris, *Inorg. Chem.,* 1995, 34, 4722.

The invention claimed is:

1. A pharmaceutical composition, for delivery of carbon monoxide to a physiological target, comprising a metal carbonyl compound or pharmaceutically acceptable salt thereof and at least one pharmaceutically acceptable carrier, wherein the metal of said metal carbonyl is bound to at least one group other than CO which is a modulator group and said metalcarbonyl makes available CO suitable for physiological effect by at least one of the following means:
   1) CO derived by dissociation of the metal carbonyl is present in the composition in dissolved form;
   2) on contact with a solvent the metal carbonyl releases CO;
   3) on contact with a tissue, organ or cell the metal carbonyl releases CO;
   4) on irradiation the metal carbonyl releases CO;
   wherein said modulator group modulates the stability of the compound and/or the release of CO from the compound.

2. A pharmaceutical composition according to claim 1, wherein the metal carbonyl compound is a complex of at least one of Fe, Mn, Ru, Rh, Ni, Mo or Co with at least one carbonyl ligand.

3. A pharmaceutical composition according to claim 1 wherein the compound or pharmaceutically acceptable salt thereof is soluble in an aqueous solvent.

4. A method of introducing CO to a mammal as a physiologically effective agent comprising the step of administering a pharmaceutical composition according to claim 1.

5. A method according to claim 4, for the stimulation of guanylate cyclase activity.

6. A method according to claim 4, for stimulating neurotransmission or vasodilation, or for the treatment of any of hypertension, radiation damage, endotoxic shock, inflammation, an inflammatory-related disease, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

7. A method according to claim 4, wherein said pharmaceutical composition is administered by an oral, intravenous, subcutaneous, nasal, inhalatory, intramuscular, intraperitoneal or suppository route.

8. A pharmaceutical composition, for delivery of carbon monoxide to a physiological target, comprising a metal carbonyl compound or pharmaceutically acceptable salt thereof and at least one pharmaceutically acceptable carrier, wherein the metal of said metal carbonyl is bound to at least one group other than CO which is a modulator group and said metal carbonyl makes available CO suitable for physiological effect by at least one of the following means:
   1) CO derived by dissociation of the metal carbonyl is present in the composition in dissolved form;
   2) on contact with a solvent the metal carbonyl releases CO;
   3) on contact with a tissue, organ or cell the metal carbonyl releases CO;
   4) on irradiation the metal carbonyl releases CO;
   wherein said modulator group modulates the stability of the compound and/or the release of CO from the compound,
   said composition being in a form administrable by at least one route selected from the group consisting of oral, intravenous, subcutaneous, nasal, inhalatory, intramuscular, intraperitoneal and suppository.

9. A pharmaceutical composition according to claim 8 wherein the compound or pharmaceutically acceptable salt thereof is soluble in an aqueous solvent.

10. A method of introducing CO to a mammal as a physiologically effective agent comprising the step of administering a pharmaceutical composition according to claim 8.

11. A method according to claim 10, for the stimulation of guanylate cyclase activity.

12. A method according to claim 10, for stimulating neurotransmission or vasodilation, or for the treatment of any of hypertension, radiation damage, endotoxic shock, inflammation, an inflammatory-related disease, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

13. A pharmaceutical composition for delivery of CO, comprising as active ingredient a compound of the formula $M(CO)_x A_y$, or a pharmaceutically acceptable salt of said compound, where x is at least one, y is at least one, M is a metal, A is selected from halogens, groups having N, P, O or S atoms providing lone electron pairs for coordination bonding to M, and conjugated carbon groups, and A is an atom or group bonded to M by an ionic, covalent or coordination bond, and in the case where y>1 each A may be the same or different.

14. A pharmaceutical composition according to claim 13 wherein M is a transition metal.

15. A pharmaceutical composition according to claim 13, wherein the compound or the pharmaceutically acceptable salt of said compound is soluble in an aqueous solvent.

16. A method of introducing CO to a mammal as a physiologically effective agent comprising the step of administering a pharmaceutical composition according to claim 13.

17. A method according to claim 16, for the stimulation of guanylate cyclase activity.

18. A method according to claim 16, for stimulating neurotransmission or vasodilation, or for the treatment of any of hypertension, radiation damage, endotoxic shock, inflammation, an inflammatory-related disease, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

19. A method according to claim 16, wherein said pharmaceutical composition is administered by an oral, intravenous, subcutaneous, nasal, inhalatory, intramuscular, intraperitoneal or suppository route.

20. A pharmaceutical composition for delivery of CO, comprising as active ingredient a compound of the formula $M(CO)_x A_y$, or a pharmaceutically acceptable salt of said compound, where x is at least one, y is at least one, M is a metal, A is selected from halogens, groups having N, P, O or S atoms providing lone electron pairs for coordination bonding to M, and conjugated carbon groups, and A is an atom or group bonded to M by an ionic, covalent or coordination bond, and in the case where y>1 each A may be the same or different,
said composition being in a form administrable by at least one route selected from the group consisting of oral, intravenous, subcutaneous, nasal, inhalatory, intramuscular, intraperitoneal and suppository.

21. A pharmaceutical composition according to claim 20 wherein M is a transition metal.

22. A pharmaceutical composition according to claim 20, wherein the compound is soluble in an aqueous solvent.

23. A method of introducing CO to a mammal as a physiologically effective agent comprising the step of administering a pharmaceutical composition according to claim 20.

24. A method according to claim 23, for the stimulation of guanylate cyclase activity.

25. A method according to claim 23, for stimulating neurotransmission or vasodilation, or for the treatment of any of hypertension, radiation damage, endotoxic shock, inflammation, an inflammatory-related disease, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

26. A pharmaceutical composition, for delivery of carbon monoxide to a physiological target, comprising a metal carbonyl compound or pharmaceutically acceptable salt thereof and at least one pharmaceutically acceptable carrier; wherein the metal of said metal carbonyl is bound to at least one group other than CO which is a modulator group and said metal carbonyl makes available CO suitable for physiological effect by at least one of the following means:
1) CO derived by dissociation of the metal carbonyl is present in the composition in dissolved form;
2) on contact with a solvent the metal carbonyl releases CO;
3) on contact with a tissue, organ or cell the metal carbonyl releases CO;
4) on irradiation the metal carbonyl releases CO;
wherein said modulator group modulates the stability of the compound and/or the release of CO from the compound, and said metal of said metal carbonyl is bound to two or three CO ligands.

27. A method of introducing CO to a mammal as a physiologically effective agent comprising the step of administering a pharmaceutical composition according to claim 26.

28. A method according to claim 27 wherein said pharmaceutical composition is administered by an oral, intravenous, subcutaneous, nasal, inhalatory, intramuscular, intraperitoneal or suppository route.

29. A pharmaceutical composition for delivery of CO, comprising as active ingredient a compound of the formula $M(CO)_x A_y$, or a pharmaceutically acceptable salt of said compound, where x is two or three, y is at least one, M is a metal, A is selected from halogens, groups having N, P, O or S atoms providing lone electron pairs for coordination bonding to M, and conjugated carbon groups, and A is an atom or group bonded to M by an ionic, covalent or coordination bond, and in the case where y>1 each A may be the same or different.

30. A method of introducing CO to a mammal as a physiologically effective agent comprising the step of administering a pharmaceutical composition according to claim 29.

31. A method according to claim 30, wherein said pharmaceutical composition is administered by an oral, intravenous, subcutaneous, nasal, inhalatory, intramuscular, intraperitoneal or suppository route.

* * * * *